US010173182B2

(12) United States Patent
Tachibana et al.

(10) Patent No.: US 10,173,182 B2
(45) Date of Patent: Jan. 8, 2019

(54) NUCLEIC ACID AMPLIFICATION DEVICE, NUCLEIC ACID AMPLIFICATION APPARATUS, AND NUCLEIC ACID AMPLIFICATION METHOD FOR TRANSPORTING REACTION SOLUTION INCLUDING TARGET NUCLEIC ACID VIA CAPILLARY FORCE TO AMPLIFY TARGET NUCLEIC ACID

(71) Applicant: PANASONIC CORPORATION, Osaka (JP)

(72) Inventors: Hiroaki Tachibana, Osaka (JP); Shogo Shibuya, Osaka (JP); Narimasa Iwamoto, Mie (JP); Eiichi Tamiya, Osaka (JP); Masato Saito, Osaka (JP); Koji Tsuji, Osaka (JP)

(73) Assignee: PANASONIC CORPORATION, Osaka (JP)

( * ) Notice: Subject to any disclaimer, the term of this patent is extended or adjusted under 35 U.S.C. 154(b) by 365 days.

(21) Appl. No.: 14/909,840

(22) PCT Filed: Aug. 8, 2014

(86) PCT No.: PCT/JP2014/004162
§ 371 (c)(1),
(2) Date: Feb. 3, 2016

(87) PCT Pub. No.: WO2015/019626
PCT Pub. Date: Feb. 12, 2015

(65) Prior Publication Data
US 2016/0199840 A1 Jul. 14, 2016

(30) Foreign Application Priority Data
Aug. 8, 2013 (JP) .................. 2013-165598

(51) Int. Cl.
C12P 19/34 (2006.01)
B01F 5/06 (2006.01)
C12Q 1/6806 (2018.01)
C12Q 1/686 (2018.01)
B01F 13/00 (2006.01)
B01L 3/00 (2006.01)
B01L 7/00 (2006.01)

(52) U.S. Cl.
CPC .......... B01F 5/0614 (2013.01); B01F 5/0647 (2013.01); B01F 13/0059 (2013.01); B01L 3/502715 (2013.01); B01L 7/525 (2013.01); C12Q 1/6806 (2013.01); C12Q 1/686 (2013.01); *B01F 2005/0636* (2013.01); *B01L 2200/06* (2013.01); *B01L 2200/10* (2013.01); *B01L 2300/0654* (2013.01); *B01L 2300/0816* (2013.01); *B01L 2300/0864* (2013.01); *B01L 2300/0867* (2013.01); *B01L 2300/0883* (2013.01); *B01L 2300/161* (2013.01); *B01L 2300/165* (2013.01); *B01L 2300/18* (2013.01); *B01L 2300/1805* (2013.01); *B01L 2300/1827* (2013.01); *B01L 2400/0406* (2013.01); *B01L 2400/086* (2013.01)

(58) Field of Classification Search
None
See application file for complete search history.

(56) References Cited

U.S. PATENT DOCUMENTS

| 7,407,630 | B2 * | 8/2008 | Reed .................... G01N 35/028 422/552 |
| 7,727,478 | B2 | 6/2010 | Higashino et al. |
| 7,833,486 | B2 | 11/2010 | Fielden et al. |
| 7,955,575 | B2 | 6/2011 | Derand et al. |
| 8,226,907 | B2 * | 7/2012 | Leach ................. B01L 3/50273 422/502 |
| 8,277,928 | B2 | 10/2012 | Opperman |
| 8,632,877 | B2 | 1/2014 | Opperman |
| 9,849,436 | B2 * | 12/2017 | Tachibana ......... B01L 3/502746 |
| 2002/0125135 | A1 | 9/2002 | Derand et al. |
| 2005/0042770 | A1 | 2/2005 | Derand et al. |
| 2005/0266448 | A1 | 12/2005 | Hagiwara et al. |
| 2006/0239861 | A1 | 10/2006 | Higashino et al. |
| 2006/0278287 | A1 | 12/2006 | Fielden et al. |

(Continued)

FOREIGN PATENT DOCUMENTS

| CN | 102899238 | 1/2013 |
| EP | 1584692 | 10/2005 |

(Continued)

OTHER PUBLICATIONS

Extended European Search Report for the corresponding European patent application No. 14835405.3, dated Jun. 21, 2016.
Office Action (including Search Report), dated Aug. 30, 2016, in the corresponding Chinese patent application No. 201480043917.8, along with an English language translation of Search Report.
Burns et al., "An Integrated Nanoliter DNA Analysis Device", Science, vol. 282, Oct. 16, 1998, pp. 484-487.
Kopp et al., "Chemical Amplification: Continuous-Flow PCR on a Chip", Science, vol. 280, May 15, 1998, pp. 1046-1048.

(Continued)

*Primary Examiner* — Kenneth R Horlick
(74) *Attorney, Agent, or Firm* — Greenblum & Bernstein, P.L.C.

(57) ABSTRACT

A nucleic acid amplification device includes: an introduction unit into which a reaction solution including a target nucleic acid is introduced; a nucleic acid amplification reaction section in which at least two temperature zones of different temperature are present, for amplifying the target nucleic acid included in the reaction solution introduced into the introduction unit; and a channel arranged to pass back and forth or in cyclic fashion through the at least two temperature zones, and having a capillary force transport mechanism for feeding the reaction solution by capillary force.

20 Claims, 34 Drawing Sheets

(56) References Cited

U.S. PATENT DOCUMENTS

| | | | |
|---|---|---|---|
| 2007/0048777 A1 | 3/2007 | Hagiwara et al. | |
| 2007/0178521 A1 | 8/2007 | Sakaino et al. | |
| 2008/0153152 A1 | 6/2008 | Wakabayashi et al. | |
| 2008/0190220 A1 | 8/2008 | Backes et al. | |
| 2008/0206848 A1 | 8/2008 | Hagiwara et al. | |
| 2008/0207892 A1 | 8/2008 | Iwaki et al. | |
| 2010/0096320 A1 | 4/2010 | Opperman | |
| 2011/0253222 A1 | 10/2011 | Arai | |
| 2013/0040374 A1 | 2/2013 | Tachibana et al. | |
| 2013/0052456 A1 | 2/2013 | Opperman | |
| 2014/0220668 A1 | 8/2014 | Tachibana et al. | |
| 2017/0175067 A1* | 6/2017 | Tachibana | C12M 23/16 |
| 2018/0056298 A1* | 3/2018 | Iwamoto | B01L 7/525 |

FOREIGN PATENT DOCUMENTS

| | | |
|---|---|---|
| EP | 2749349 | 7/2014 |
| JP | 09-262084 | 10/1997 |
| JP | 2001-252896 | 9/2001 |
| JP | 2002-018271 | 1/2002 |
| JP | 2002-335960 | 11/2002 |
| JP | 2003-518610 | 6/2003 |
| JP | 2004-340895 | 12/2004 |
| JP | 2005-125280 | 5/2005 |
| JP | 2005-295877 | 10/2005 |
| JP | 2005-345279 | 12/2005 |
| JP | 2006-058280 | 3/2006 |
| JP | 2006-266923 | 10/2006 |
| JP | 2007-502428 | 2/2007 |
| JP | 2007-064742 | 3/2007 |
| JP | 2007-085998 | 4/2007 |
| JP | 2007-292506 | 11/2007 |
| JP | 2008-148690 | 7/2008 |
| JP | 2008-151771 | 7/2008 |
| JP | 2008-525768 | 7/2008 |
| JP | 2008-203003 | 9/2008 |
| JP | 2009-514674 | 4/2009 |
| JP | 2013-055921 | 3/2013 |
| JP | 2013-226497 | 11/2013 |
| WO | 01/47637 | 7/2001 |
| WO | 2004/103891 | 12/2004 |
| WO | 2006/069757 | 7/2006 |
| WO | 2007/056338 | 5/2007 |
| WO | 2008/044387 | 4/2008 |
| WO | 2010/061598 | 6/2010 |
| WO | 2011/136344 | 11/2011 |
| WO | 2012/103533 | 8/2012 |
| WO | 2013/027393 | 2/2013 |

OTHER PUBLICATIONS

Tachibana et al., "Capillary-driven continuous-flow PCR microfluidic device for rapid pathogen gene detection", The Chemical Society of Japan, Mar. 12, 2014, 3 G2-51.

International Search Report issued in PCT/JP2014/004162, dated Oct. 7, 2014.

* cited by examiner

FIG. 9
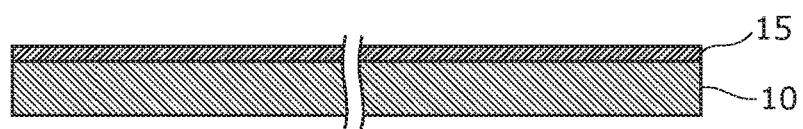
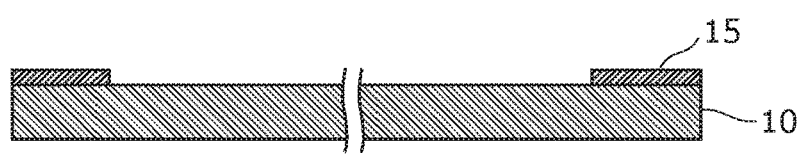
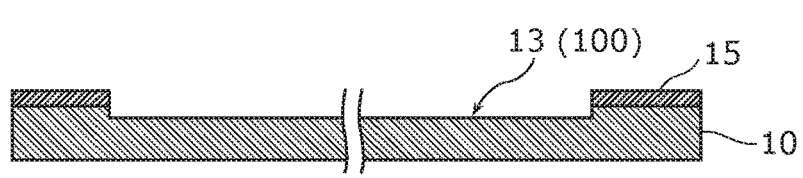
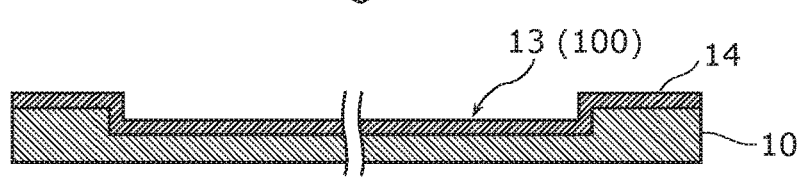
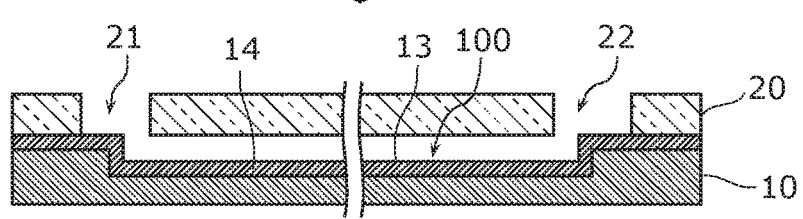

|  |  | Temperature (°C) | Viscosity (Pa·s) | Capillary Force (kPa) |
|---|---|---|---|---|
| No1 | PCR Solution 1 (Experiment) | 25 | 0.0019 | 5.8 |
| No2 | PCR Solution 2 (Experiment) | 60 | 0.0010 | 4.9 |
| No3 | PCR Solution 3 (Experiment) | 95 | 0.00061 | 3.9 |
| No4 | Deionized Water (Experiment) | 25 | 0.00099 | 4.4 |
| No5 | Deionized Water (Theory) | 25 | 0.00089 | 4.3 |

(i) Region in which fluid front of solution is in nucleic acid amplification reaction section (ii) Region in which fluid front of solution is in fed solution retention section

NUCLEIC ACID AMPLIFICATION DEVICE, NUCLEIC ACID AMPLIFICATION APPARATUS, AND NUCLEIC ACID AMPLIFICATION METHOD FOR TRANSPORTING REACTION SOLUTION INCLUDING TARGET NUCLEIC ACID VIA CAPILLARY FORCE TO AMPLIFY TARGET NUCLEIC ACID

TECHNICAL FIELD

The present invention relates to a nucleic acid amplification device, a nucleic acid amplification apparatus using the nucleic acid amplification device, and a nucleic acid amplification method.

BACKGROUND ART

A nucleic acid amplification device is a device for amplifying a sample of a target nucleic acid, and, for example, amplifies a target nucleic acid by repeatedly subjecting a reaction solution (reaction fluid) including the target nucleic acid to desired temperature changes.

Moreover, use of a microfluidic device is a known method for rapidly inducing temperature changes in the reaction solution. The microfluidic device is a device capable of inducing chemical reaction of a reaction solution including an extremely small amount of a sample and reagent, and examples include a microreaction device (microreactor), an integrated DNA device, and a microelectrophoresis device.

For example, Patent Literature (PTL) 1 and Non Patent Literature (NPL) 1 disclose dividing a device into a plurality of different temperature zones and providing channels (meandering channels) that meander such that the reaction solution repeatedly flows through the temperature zones. Since this configuration makes it possible to speed up the temperature changes induced in the reaction solution in the channel, when a solution including nucleic acid is used as the reaction solution, nucleic acid amplification of the nucleic acid can be performed rapidly.

CITATION LIST

Patent Literature

[PTL 1] Japanese Unexamined Patent Application Publication No. 2002-18271

Non Patent Literature

[NPL 1] Science, vol. 280, pp. 1046-1048 (1998)

SUMMARY OF INVENTION

Technical Problem

However, with the above-described conventional microfluidic device, use of an external pump such as a syringe pump to advance the reaction solution in the channel is required. Use of an external pump is accompanied by problems such as the need to connect the pump and the channel together by hand, an increase in the size of the system, and an increase in cost.

The present invention was conceived to solve the above-described problem and has an object to provide, for example, a nucleic acid amplification device that can advance the reaction solution in the channel without the use of a pump.

Solution to Problem

In order to achieve the above-described object, one aspect of the nucleic acid amplification device according to the present invention includes: an introduction unit into which a reaction solution including a target nucleic acid is introduced; a nucleic acid amplification reaction section in which at least two temperature zones of different temperature are present, for amplifying the target nucleic acid included in the reaction solution introduced into the introduction unit; and a channel arranged to pass back and forth or in cyclic fashion through the at least two temperature zones, and having a capillary force transport mechanism for feeding the reaction solution by capillary force.

Moreover, in one aspect, the nucleic acid amplification device according to the present invention may further include a discharge unit configured to discharge the reaction solution including the target nucleic acid after amplification, wherein wall surfaces of the channel may enclose an entire perimeter of the channel in a cross section taken perpendicular to a feeding direction of the reaction solution, and the channel may be connected to an external space only in the introduction unit and the discharge unit.

Moreover, in one aspect of the nucleic acid amplification device according to the present invention, the channel may have, as the capillary force transport mechanism, a wall surface that is a hydrophilic surface and has an acute contact angle.

Moreover, in one aspect of the nucleic acid amplification device according to the present invention, wall surfaces around an entire perimeter of the channel in a cross section taken perpendicular to a feeding direction of the reaction solution may be hydrophilic surfaces.

Moreover, in one aspect of the nucleic acid amplification device according to the present invention, the hydrophilic surface of the channel may be a surface of a hydrophilic film formed in the channel.

In this case, the hydrophilic film may be formed of a material including a hydrophilic group and a hydrophobic group.

Moreover, in one aspect of the nucleic acid amplification device according to the present invention, the hydrophilic film may be formed by a surfactant.

In this case, the surfactant may be a non-ionic surfactant.

Moreover, in one aspect, the nucleic acid amplification device according to the present invention may further include a fed solution retention section for retaining the reaction solution, wherein the channel may include a first channel disposed in the nucleic acid amplification reaction section and a second channel disposed in the fed solution retention section, and the second channel may retain the reaction solution fed from the first channel.

In this case, the volumetric capacity of the second channel may be 10% or more of the total volumetric capacity of the channel.

Moreover, in one aspect of the nucleic acid amplification device according to the present invention, at least two temperature zones of different temperature may be present in the nucleic acid amplification reaction section.

Moreover, in one aspect of the nucleic acid amplification device according to the present invention, the channel may be arranged to pass back and forth or in cyclic fashion through the at least two temperature zones.

Moreover, in one aspect of the nucleic acid amplification device according to the present invention, the temperature of each temperature zone in the two or more temperature zones may be set by a heater.

Moreover, in one aspect of the nucleic acid amplification device according to the present invention, the introduction unit may include a plurality of introduction units, the nucleic acid amplification device may further include a mixing unit disposed between the nucleic acid amplification reaction section and the plurality of introduction units, the plurality of introduction units may be connected as one in the mixing unit via introduction channels corresponding to the plurality of introduction units, and a plurality of solutions introduced via the plurality of introduction units may mix together in the mixing unit to produce the reaction solution.

Moreover, in one aspect of the nucleic acid amplification device according to the present invention, the plurality of solutions introduced via the plurality of introduction units may be mixed together in the mixing unit by diffusion.

Moreover, in one aspect of the nucleic acid amplification device according to the present invention, in the mixing unit, the channel may be a meandering channel.

Moreover, in one aspect of the nucleic acid amplification device according to the present invention, in the mixing unit, the channel may have a section having a cross-sectional area that sectionally decreases.

Moreover, in one aspect of the nucleic acid amplification device according to the present invention, the plurality of solutions introduced via the plurality of introduction units may be mixed together in the mixing unit by helicoidal flow.

Moreover, in one aspect of the nucleic acid amplification device according to the present invention, in the mixing unit, the channel may be a loop-shaped channel.

Moreover, in one aspect of the nucleic acid amplification device according to the present invention, the channel may include, at least in the nucleic acid amplification reaction section, a region having a cross-sectional area that decreases in the feeding direction.

Moreover, in one aspect of the nucleic acid amplification device according to the present invention, in the region where the cross-sectional area decreases, the channel may have a tapered structure.

Moreover, in one aspect of the nucleic acid amplification device according to the present invention, in the region where the cross-sectional area decreases, the channel may be formed of a plurality of lines in a meandering arrangement and may have a cross-sectional area that decreases with each line in the feeding direction.

Moreover, in one aspect of the nucleic acid amplification device according to the present invention, in the region where the cross-sectional area decreases, the cross-sectional area of the channel may be adjusted with pillars disposed in the channel.

Moreover, in one aspect of the nucleic acid amplification device according to the present invention, a portion of the channel may be divided into branches.

Moreover, in one aspect of the nucleic acid amplification device according to the present invention, in the region where the cross-sectional area decreases, the channel may have a constant depth.

Moreover, in one aspect, the nucleic acid amplification apparatus according to the present invention is a nucleic acid amplification apparatus including the nucleic acid amplification device according to any one of the above descriptions, and includes a temperature control unit configured to control a temperature of the nucleic acid amplification reaction section.

Moreover, in one aspect, the nucleic acid amplification apparatus according to the present invention may further include a detection unit configured to detect nucleic acid amplification of the target nucleic acid.

Moreover, in one aspect of the nucleic acid amplification apparatus according to the present invention, the detection unit may include a light output unit configured to output light for irradiating the nucleic acid amplification device; and a light receptor unit configured to receive reflected light of the light irradiating the nucleic acid amplification device.

Moreover, in one aspect of the nucleic acid amplification apparatus according to the present invention, the detection unit may further include an optical scanning unit configured to scan the light over the channel of the nucleic acid amplification device.

Moreover, in one aspect, the nucleic acid amplification method according to the present invention is a nucleic acid amplification method for amplifying a target nucleic acid using a nucleic acid amplification device and includes: introducing the target nucleic acid and a reagent for amplifying the target nucleic acid into the nucleic acid amplification device; and as a reaction solution including the target nucleic acid and the reagent is fed by capillary force, amplifying the target nucleic acid included in the reaction solution.

Moreover, in one aspect of the nucleic acid amplification method according to the present invention, in the introducing, a premixed solution of (i) a solution including the target nucleic acid and (ii) the reagent may be introduced into the nucleic acid amplification device as the reaction solution.

Moreover, in one aspect of the nucleic acid amplification method according to the present invention, in the introducing, a first solution including the target nucleic acid and a second solution including the reagent may be separately introduced into the nucleic acid amplification device, and in the amplifying, as a solution of the first solution and the second solution mixed together in the nucleic acid amplification device is fed by capillary force as the reaction solution, the target nucleic acid included in the reaction solution may be amplified.

Moreover, in one aspect of the nucleic acid amplification method according to the present invention, in the amplifying, the target nucleic acid included in the reaction solution may be amplified by subjecting the reaction solution to cyclic temperature changes.

Moreover, in one aspect of the nucleic acid amplification method according to the present invention, the nucleic acid amplification device may include a discharge unit that discharges the reaction solution including the target nucleic acid after amplification, and when a fluid front of the reaction solution fed by capillary force reaches the discharge unit, introduction of a solution including the target nucleic acid into the introduction unit may be interrupted.

Advantageous Effects of Invention

According to the present invention, a reaction solution can be advanced in the channel without the use of a pump.

BRIEF DESCRIPTION OF DRAWINGS

FIG. 9 illustrates in (a)-(e) cross sectional views of a nucleic acid amplification device according to Embodiment 1 of the present invention to illustrate the flow of the manufacturing method of the nucleic acid amplification device.

DESCRIPTION OF EMBODIMENTS

Figure 1:
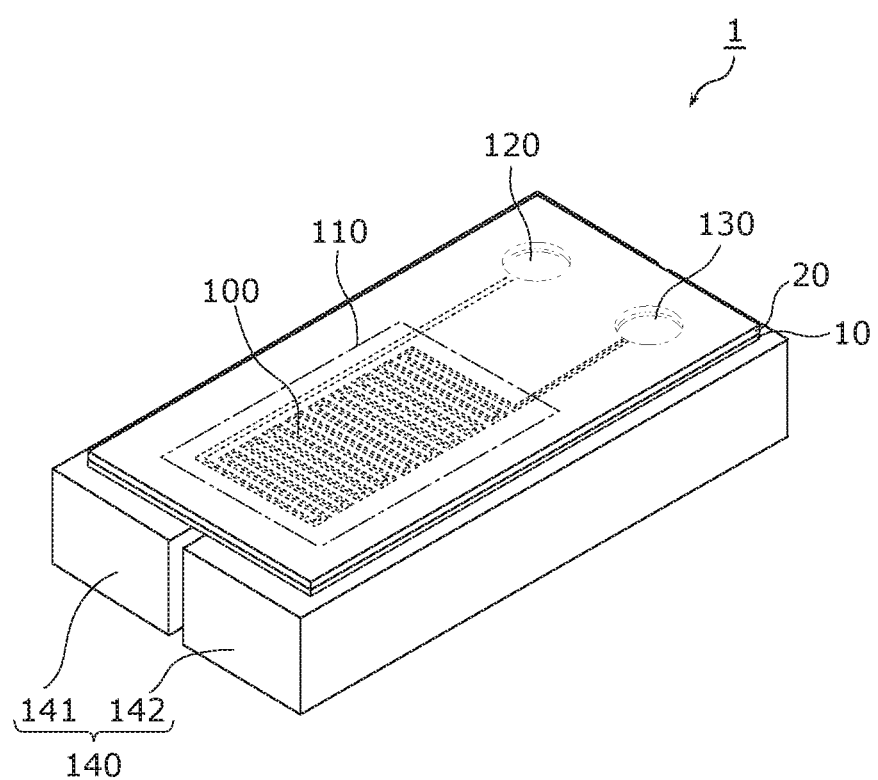
FIG. 1 is a perspective view of a nucleic acid amplification device according to Embodiment 1 of the present invention.

Hereinafter, embodiments of present invention are described with reference to the Drawings. Note that the embodiments described below each show a specific, preferred example of the present invention. Therefore, the numerical values, shapes, materials, elements, arrangement and connection of the elements, steps, order of the steps, etc., shown in the following embodiments are mere examples, and are not intended to limit the present invention. Consequently, those elements in the following embodiments not recited in any one of the independent claims, which indicate the broadest concepts of the present disclosure, are described as arbitrary elements.

Note that the respective figures are schematic diagrams and are not necessarily precise illustrations. Additionally, components that are essentially the same share like reference numerals in the figures, and overlapping explanations thereof are omitted or simplified.

Embodiment 1

Figure 2:
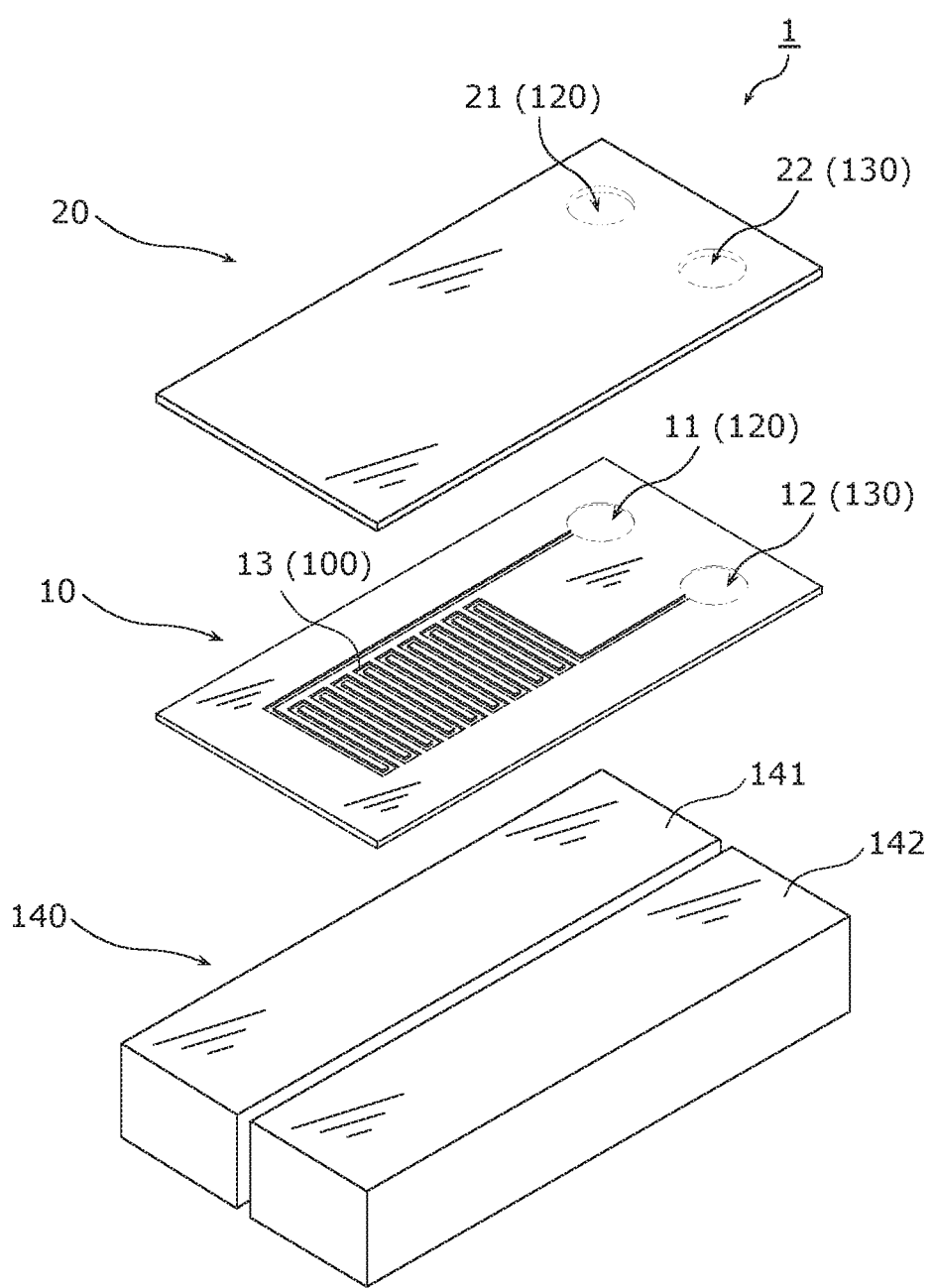
FIG. 2 is an exploded perspective view of a nucleic acid amplification device according to Embodiment 1 of the present invention.
Figure 3:
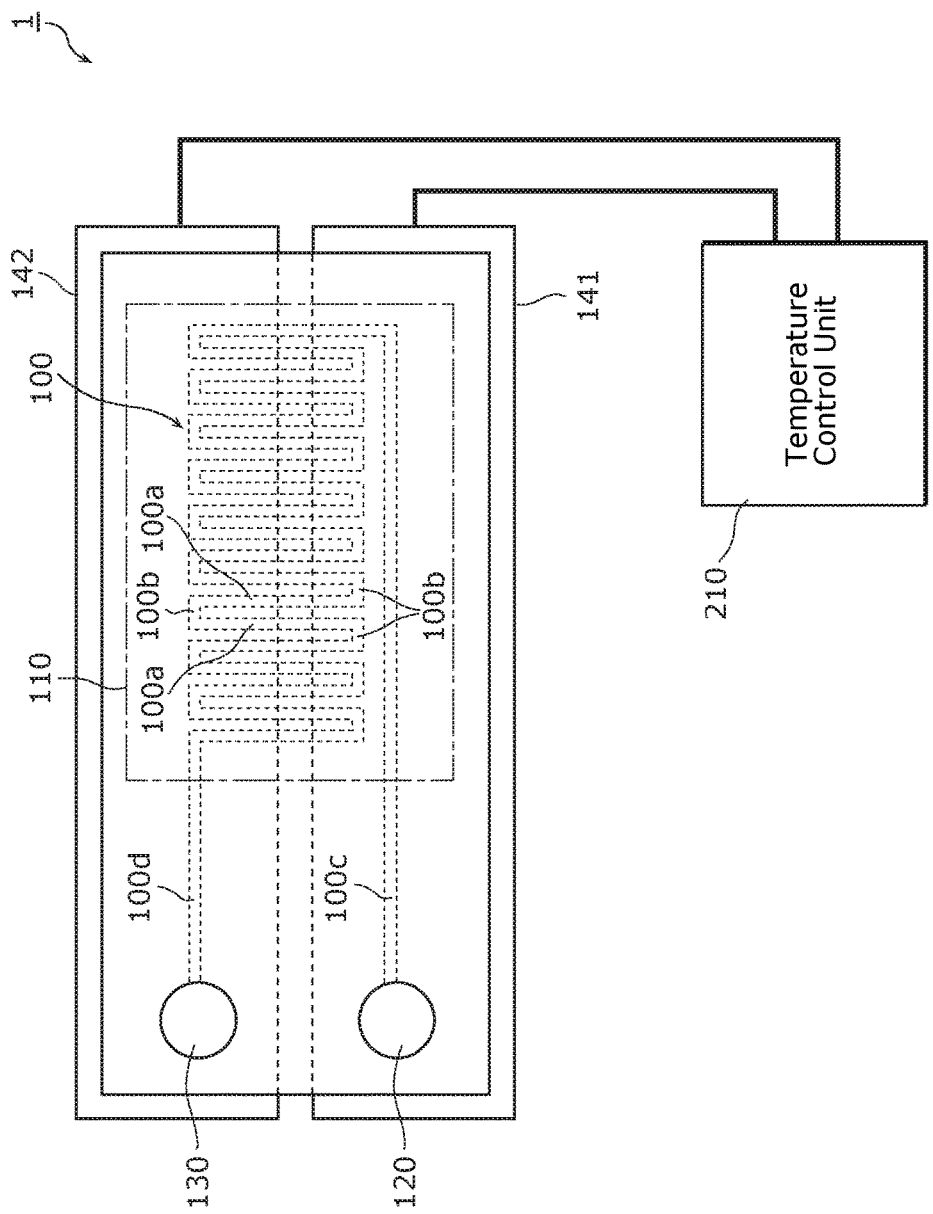
FIG. 3 is a plan view of a nucleic acid amplification device according to Embodiment 1 of the present invention.
Figure 4:
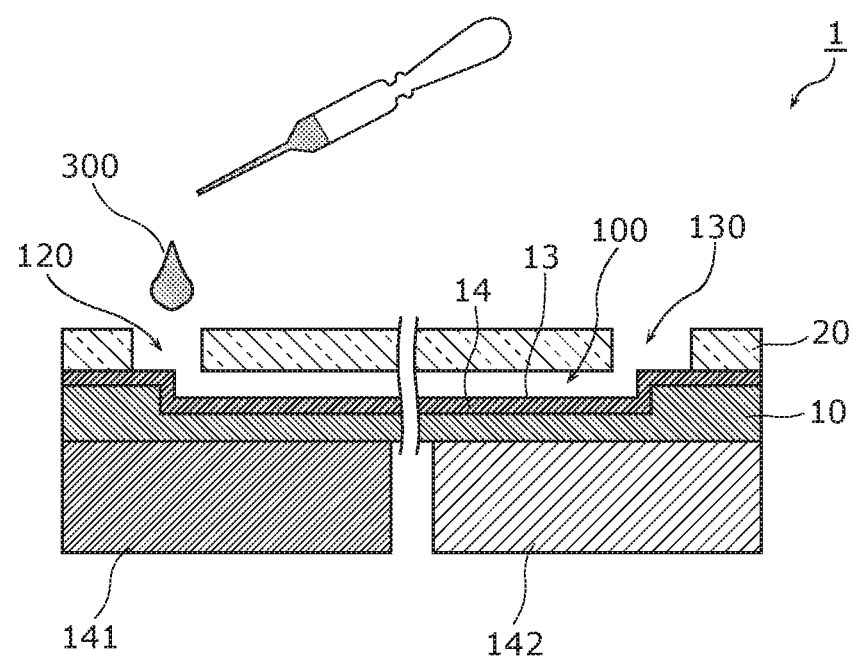
FIG. 4 is a cross sectional view of a nucleic acid amplification device according to Embodiment 1 of the present invention.

First, the configuration of the nucleic acid amplification device 1 according to Embodiment 1 of the present invention will be described using FIG. 1 through FIG. 4. FIG. 1 is a perspective view of the nucleic acid amplification device according to Embodiment 1 of the present invention, FIG. 2 is an exploded perspective view of the same nucleic acid amplification device, FIG. 3 is a plan view of the same nucleic acid amplification device, and FIG. 4 is a cross sectional view of the same nucleic acid amplification device.

As illustrated in FIG. 1 through FIG. 4, the nucleic acid amplification device 1 according to the present embodiment is a device (device chip) for amplifying a target nucleic acid sample, and includes an introduction unit (inlet) 120 into which a reaction solution including at least the target nucleic acid is introduced, a nucleic acid amplification reaction section 110 for amplifying the target nucleic acid included in the reaction solution introduced into the introduction unit 120, a discharge unit (drain) 130 for discharging the reaction solution including the target nucleic acid amplified in the nucleic acid amplification reaction section 110, and a heater unit 140 for heating the reaction solution including the target nucleic acid.

The nucleic acid amplification reaction section 110 further includes a channel 100 including a capillary force transport mechanism for feeding the introduced reaction solution by capillary force. The channel 100 is a reaction channel through which the reaction solution flows one-way, and is configured to pass through at least the nucleic acid amplification reaction section 110. The channel 100 according to present embodiment is configured of a single channel, and one end of the channel is connected to the introduction unit 120 and the other end of the channel is connected to the discharge unit 130.

In the nucleic acid amplification reaction section 110, the target nucleic acid included in the reaction solution is amplified as the reaction solution is fed through the channel 100 by capillary force. The reaction solution (reaction fluid) is a solution including at least a target nucleic acid sample, and in present embodiment, is an aqueous solution including the target nucleic acid and a reagent for amplifying the target nucleic acid. Note that the reaction solution may include, for example, some type of alcohol or a surfactant.

The polymerase chain reaction (PCR) method will be used with the nucleic acid amplification device 1 in the example given in the present embodiment. The PCR method is a technique of amplifying DNA with a temperature cycle. In addition to the target DNA, the reaction solution includes, for example, a PCR primer, a polymerase enzyme, and a buffer. Subjecting this sort of reaction solution to a temperature cycle makes it possible to amplify the DNA. The amount of amplification of the amplified DNA can be detected by a reaction detection mechanism.

More specifically, the nucleic acid amplification device 1 is configured of a first substrate 10, a second substrate 20, and the heater unit 140. Moreover, the heater unit 140 includes a first heater block 141 and a second heater block 142 which have different set temperatures.

The nucleic acid amplification device 1 according to the present embodiment is a microfluidic device that includes a micro channel (the channel 100). The silhouette of the nucleic acid amplification device 1 is, for example, a 40 mm long by 20 mm wide approximate rectangle.

Hereinafter, each element in the nucleic acid amplification device 1 will be described in detail using FIG. 1 through FIG. 4.

[First Substrate]

As illustrated in FIG. 2, the first substrate 10 includes a first recessed portion 11 that forms part of the introduction unit 120, a second recessed portion 12 that forms part of the discharge unit 130, and a groove 13 that forms the channel 100. The first substrate 10 is, for example, a silicon substrate.

The groove 13 (the channel 100) is formed so as to connect the first recessed portion 11 and the second recessed portion 12. The reaction solution flows in the groove 13 (the channel 100). More specifically, when the reaction solution is introduced into the first recessed portion 11 (the introduction unit 120), the reaction solution advances through the groove 13 (the channel 100) toward the second recessed portion 12 (the discharge unit 130).

As illustrated in FIG. 3, the portion of the channel 100 in the nucleic acid amplification reaction section 110 is a meandering channel formed so as to meander in such a manner as to alternately pass through the first heater block 141 (the first temperature zone) and the second heater block 142 (the second temperature zone) repeatedly.

More specifically, the portion of the channel 100 in the nucleic acid amplification reaction section 110 is formed so as to continuously bend back on itself (run back and forth) at bends located at predetermined intervals in the line-shaped channel. The number of times the portion of the channel 100 in the nucleic acid amplification reaction section 110 bends back on itself is equivalent to about 20 to 70 cycles. As one example, the length of the channel 100 per cycle (the length of one main channel 100*a*) can be 32 mm.

The channel 100 according to the present embodiment includes a plurality of line-shaped main channels 100*a* of a predetermined length and sub channels 100*b* that connect two ends adjacent rows of the main channels 100*a*. The main channels 100*a* and the sub channels 100*b* are disposed in the nucleic acid amplification reaction section 110.

The main channels 100a are disposed approximately perpendicular to the lengthwise direction of the first heater block 141 and the second heater block 142 in such a manner as to bridge the first heater block 141 and the second heater block 142. The sub channels 100b are disposed approximately parallel to the lengthwise direction of the first heater block 141 and the second heater block 142.

Note that the channel 100 further includes an introduction channel 100c that is a channel for guiding the reaction solution from the introduction unit 120 to the nucleic acid amplification reaction section 110, and a discharge channel 100d for guiding the reaction solution from the nucleic acid amplification reaction section 110 to the discharge unit 130.

The starting end of the introduction channel 100c is the entrance for the entire channel 100, and the terminal end of the introduction channel 100c is the entrance for the portion of the channel 100 in the nucleic acid amplification reaction section. The starting end of discharge channel 100d is the exit for the portion of the channel 100 in the nucleic acid amplification reaction section, and the terminal end of the discharge channel 100d is the exit for the entire channel 100.

As illustrated in FIG. 4, a hydrophilic film 14, such as a silicon oxide film, is formed on the inner surface of the groove 13 forming the channel 100. Forming the hydrophilic film 14 makes the wall surface of the channel 100 (the groove 13) hydrophilic. In the present embodiment, the hydrophilic film 14 is formed as the capillary force transport mechanism on each of the main channels 100a, the sub channels 100b, the introduction channel 100c, and the discharge channel 100d.

The channel 100 configured in this way is a micro channel, and, for example, has a rectangular cross sectional shape. In this case, the channel width (groove width) of the groove 13 forming the channel 100 is, for example, about 20 to 300 µm, and the depth of the groove 13 is about 50 to 150 µm.

Note that the cross sectional shape of the groove 13 is not limited to a rectangular shape, and may be a semicircle or inverted triangle. Moreover, the first recessed portion 11 and the second recessed portion 12 can be recessed portions having circular openings, for example. The first substrate 10 may be either one of a light-transmissive substrate such as a transparent substrate, or an opaque substrate, and, moreover, the first substrate 10 is not limited to a silicon substrate, and may be a resin substrate or a glass substrate, for example.

[Second Substrate]

As illustrated in FIG. 1, the second substrate 20 is a lid that covers the first substrate 10 and is disposed on the first substrate 10. The second substrate 20 is, for example, a transparent resin substrate or a glass substrate.

As illustrated in FIG. 2, the second substrate 20 includes, as part of the introduction unit 120, a first through-hole 21 that opens through the second substrate 20. The second substrate 20 also includes, as part of the discharge unit 130, a second through-hole 22 that opens through the second substrate 20. The first through-hole 21 and the second through-hole 22 are through-holes having, for example, a circular opening.

As illustrated in FIG. 4, by placing the second substrate 20 on the first substrate 10, the opening of the groove 13 is sealed whereby the channel 100 is sealed in all directions. With this, the wall surfaces of the channel 100 enclose an entire perimeter of the channel 100 in a cross section taken perpendicular to the feeding direction (traveling direction) of the reaction solution, and the channel 100 is connected to an external space only in the introduction unit 120 and the discharge unit 130. Here, by enclosing the channel 100 in all directions, capillary force in the channel 100 can be increased and the reaction solution can be inhibited from volatilizing while being fed.

Note that the material of the second substrate 20 is not limited to resin or glass, and may be silicon, for example.

[Heater Unit]

As illustrated in FIG. 1 through FIG. 3, the heater unit 140 is disposed in at least the nucleic acid amplification reaction section 110, and the reaction solution fed through the portion of the channel 100 in the nucleic acid amplification reaction section 110 is subjected to a predetermined temperature by the heater unit 140.

In the present embodiment, as the heater unit 140, the first heater block 141 and the second heater block 142, which are set at predetermined different temperatures, are located in the nucleic acid amplification reaction section 110. In other words, the two heater blocks—the first heater block 141 and the second heater block 142—form two temperature zones set at predetermined different temperatures in the nucleic acid amplification reaction section 110.

Note that the first heater block 141 and the second heater block 142 are, for example, heaters using cuboid blocks of metal such as aluminum or stainless steel. Other than heater blocks, metal thin film heaters formed by printing a metal thin film on a glass substrate, for example, can be used as the heater unit 140.

The region in which the first heater block 141 set at a first temperature is located is a first temperature zone. The region in which the second heater block 142 set at a second temperature is located is a second temperature zone different from the first temperature zone.

In the present embodiment, the temperature of the first heater block 141 is set higher than the temperature of the second heater block 142. In other words, the region in which the first heater block 141 is located is a high temperature zone, and the region in which the second heater block 142 is located is a low temperature zone.

The temperature of the first heater block 141, which is the high temperature zone, is, for example, 93° C. to 98° C., and in the present embodiment, is set to approximately 95° C., which is the temperature at which denaturation of the nucleic acid amplification reaction occurs. The temperature of the second heater block 142, which is the low temperature zone, is, for example, 50° C. to 75° C., and in the present embodiment, is set to approximately 60° C., which is the temperature at which annealing and extension occurs.

As illustrated in FIG. 3, the heater unit 140 is connected to a temperature control unit 210. With this, the temperatures of the first heater block 141 and the second heater block 142 can be controlled by the temperature control unit 210.

The first heater block 141 and the second heater block 142 are lined up with a predetermined space between them. The first substrate 10 is disposed on the first heater block 141 and the second heater block 142. More specifically, the first substrate 10 is placed on the heater unit 140 so that the main channels 100a of the channel 100 bridge the first heater block 141 and the second heater block 142. With this, the channel 100 is configured to pass back and forth through the two temperature zones in a plurality of cycles.

Figure 5:
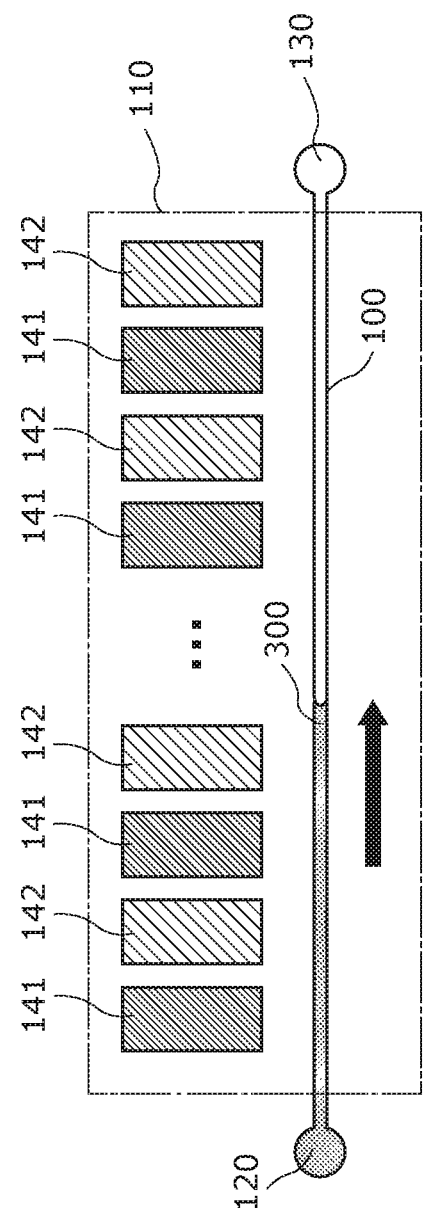
FIG. 5 is for illustrating the temperature cycle in a nucleic acid amplification device according to Embodiment 1 of the present invention.

With this configuration, as illustrated in FIG. 5, when the reaction solution 300 is introduced via the introduction unit 120, the reaction solution 300 is fed to the discharge unit 130 in such a manner as to alternately pass through the two temperature zones (the first heater block 141 and the second heater block 142) in the nucleic acid amplification reaction section 110 repeatedly. In other words, the reaction solution 300 flowing through the channel 100 can be subjected to a heat cycle.

With the nucleic acid amplification device 1 according to the present embodiment, since the reaction solution can be fed by capillary force due to the capillary force transport mechanism of the channel 100, the reaction solution can be advanced in the channel without the use of an external pump such as a syringe pump. Consequently, nucleic acid amplification of the target nucleic acid can be performed at low cost and easily.

[Characteristics of Nucleic Acid Amplification Method and Nucleic Acid Amplification Device]

Figure 6:
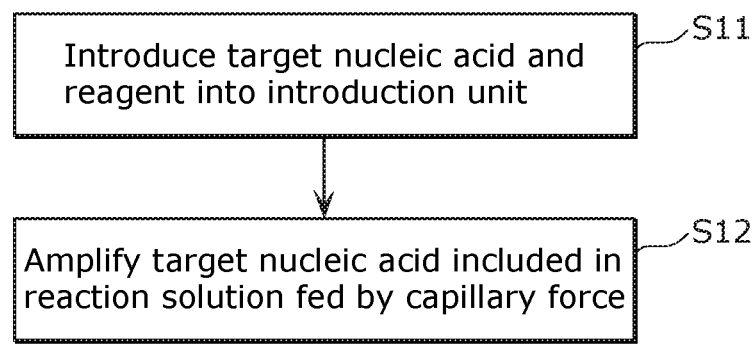
FIG. 6 is a flow chart of a nucleic acid amplification method according to Embodiment 1 of the present invention.
Figure 7A:
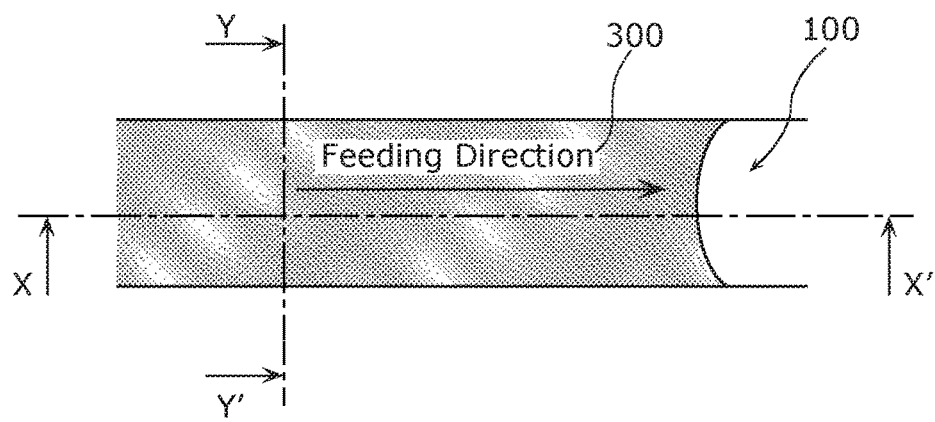
FIG. 7A is a plan view of a channel in a nucleic acid amplification device according to Embodiment 1 of the present invention.
Figure 7B:
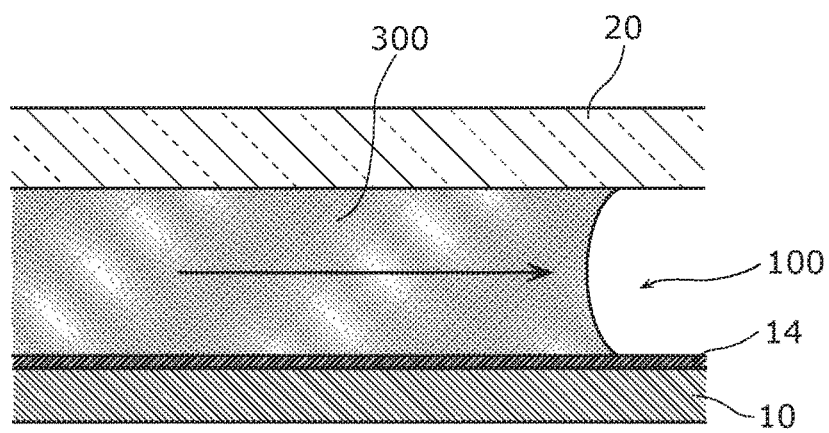
FIG. 7B is a cross sectional view of a channel of a nucleic acid amplification device according to Embodiment 1 of the present invention, taken along line X-X' in FIG. 7A.
Figure 7C:
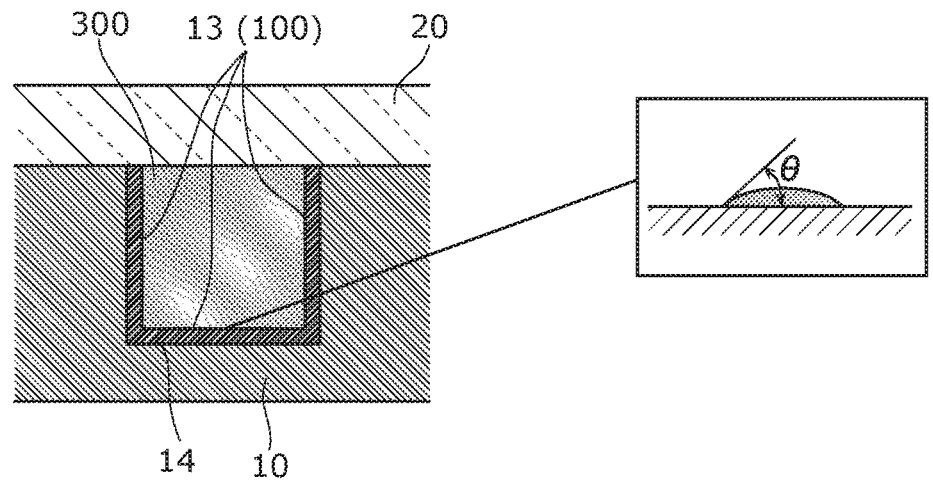
FIG. 7C is a cross sectional view of a channel of a nucleic acid amplification device according to Embodiment 1 of the present invention, taken along line Y-Y' in FIG. 7A.

Next, the characteristics of the nucleic acid amplification method and the nucleic acid amplification device according to Embodiment 1 of the present invention will be described using FIG. 6 and FIG. 7A through FIG. 7C, with reference to FIG. 1 through FIG. 5. FIG. 6 is a flow chart of a nucleic acid amplification method according to Embodiment 1 of the present invention. FIG. 7A through FIG. 7C illustrate a channel of the nucleic acid amplification device according to Embodiment 1 of the present invention, where FIG. 7A is a plan view, FIG. 7B is a cross sectional view taken along line X-X' in FIG. 7A, and FIG. 7C is a cross sectional view taken along line Y-Y' in FIG. 7A.

As illustrated in FIG. 6, the nucleic acid amplification method according to the present embodiment is a method for amplifying a target nucleic acid using the above-described nucleic acid amplification device 1, and includes: introducing the target nucleic acid sample and a reagent for amplifying the target nucleic acid into the introduction unit 120 of the nucleic acid amplification device 1 (step S11); and as a reaction solution including the target nucleic acid and the reagent is fed by capillary force, amplifying the target nucleic acid included in the reaction solution (step S12).

With this, since the reaction solution can be fed by capillary force, the reaction solution can be easily fed without the use of an external pump such as a syringe pump. Consequently, nucleic acid amplification of the target nucleic acid can be performed at low cost.

Moreover, in the present embodiment, in the above-described introducing (step S11), a premixed solution including the reagent and the reaction solution, which includes the target nucleic acid, is introduced into the introduction unit 120 of the nucleic acid amplification device 1 as the reaction solution. For example, as illustrated in FIG. 4, a pipette is used to dispense the reaction solution 300 into the introduction unit 120.

The reaction solution introduced into the introduction unit 120 is fed from the introduction unit 120 to the nucleic acid amplification reaction section 110 via the channel 100 (the introduction channel 100c).

Moreover, in the present embodiment, in the above-described amplifying (step S12), the target nucleic acid included in the reaction solution is amplified by subjecting the reaction solution to cyclic temperature changes.

More specifically, the reaction solution reaching the nucleic acid amplification reaction section 110 repeatedly passes back and forth through the first heater block 141 and the second heater block 142 as it passes through the main channels 100a and the sub channels 100b. In other words, since the reaction solution passes back and forth through the high temperature zone (the first heater block 141) and the low temperature zone (the second heater block 142) of the heater unit 140 as it is fed, the reaction solution is alternately and repeatedly heated and cooled. With this, since the reaction solution 300 flowing through the channel 100 can be subjected to a heat cycle, the target nucleic acid included in the reaction solution is amplified as a result of repeated denaturation in the high temperature zone and annealing and extension in the low temperature zone, in this way, since the temperature of the reaction solution can be increased and decreased as the reaction solution is fed, substantially rapid PCR by flow can be achieved. Thus, the target nucleic acid included in the reaction solution can be rapidly amplified.

Next, the reaction solution is fed from the nucleic acid amplification reaction section 110 to the discharge unit 130 via the discharge channel 100d. In the present embodiment, when the fluid front of the reaction solution introduced into the introduction unit 120 reaches the discharge unit 130, introduction of the solution including the target nucleic acid (referred to as the reaction solution in the present embodiment) into the introduction unit 120 is interrupted, which results in the channel 100 being filled with the reaction solution. In other words, in the present embodiment, the reaction solution is subjected to temperature changes as the reaction solution is fed by capillary force, and when the reaction solution reaches the discharge unit 130, chemical reaction of the reaction solution is completed. Note that the reaction solution reaching the discharge unit 130 may be replaced together with the first substrate 10 instead of being discharged from the discharge unit 130, but the reaction solution may be discharged from the discharge unit 130 as needed.

In this way, the reaction solution advances through the channel 100. Here, in the present embodiment, as illustrated in FIG. 7A through FIG. 7C, the channel 100 includes a hydrophilic wall surface with an acute contact angle θ as the capillary force transport mechanism that feeds the reaction solution 300 by capillary force.

More specifically, as illustrated in FIG. 7C, the hydrophilic film 14 having a hydrophilic surface is formed on the three wall surfaces of the bottom section and both side sections of the groove 13 in a cross section taken perpendicular to the feeding direction of the reaction solution 300. Forming the hydrophilic film 14 makes the surfaces of the groove 13 hydrophilic, giving the inner wall surfaces of the channel 100 a hydrophilic surface. The hydrophilic film 14 can be formed in the groove 13 by surface treating the groove 13.

Giving the inner wall surfaces of the channel 100 a hydrophilic surface allows for the reaction solution to be fed smoothly, and makes it possible to inhibit the generation of air bubbles as well as accurately amplify the target nucleic acid included in the reaction solution.

The hydrophilic film 14 may, for example, be formed of a material containing hydrophilic groups and hydrophobic groups. When the hydrophilic film 14 contains hydrophobic groups, the hydrophilic film 14 can easily be formed on the inner wall surfaces of the groove 13. More specifically, when the first substrate 10 is a resin substrate or a similar substrate and the exposed surfaces of the groove 13 are hydrophobic surfaces, the hydrophobic groups of the hydrophilic film 14 easily attach to the hydrophobic surfaces of the groove 13, which makes it easy to form the hydrophilic film 14 on the surfaces of the groove 13.

As such, a surfactant may be used as the material for the hydrophilic film 14 containing hydrophilic groups and hydrophobic groups. With this, the hydrophilic film 14 can easily be formed on the surfaces of the groove 13.

In this case, a non-ionic surfactant in particular may be used as the hydrophilic film 14. With this, since this reduces inhibition of a chemical reaction of the reaction solution, the target nucleic acid included in the reaction solution can be accurately amplified.

Tween 20 (Polyoxyethylene (20) Sorbitan Monolaurate) represented by the compositional formula in (Formula 1) below can be used as this sort of surfactant.

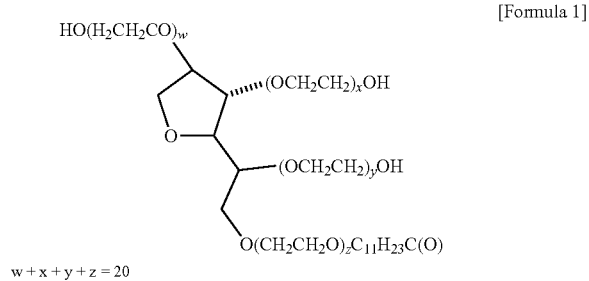

[Formula 1]

w + x + y + z = 20

Additionally, the surfactants Nonident P-40 (Octylphenyl-polyethylene glycol) or Triton X-100 (Polyoxyethylene (10) Octylphenyl Ether) represented by the compositional formulas in (Formula 2) and (Formula 3) below can be used as the material for the hydrophilic film 14.

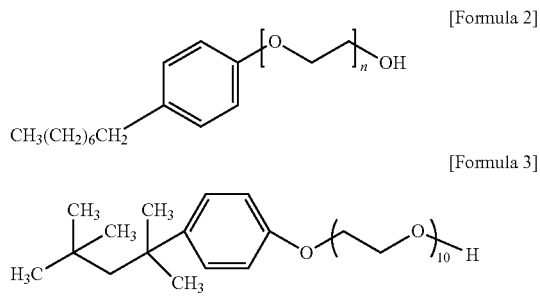

[Formula 2]

[Formula 3]

Each of the surfactants Tween 20, Nonident P-40, and Triton X-100 is a liquid at room temperature.

When these surfactants are used as the material for the hydrophilic film 14, the following method can be used to form the hydrophilic film 14 in the groove 13.

For example, a solution of an above surfactant dissolved in a solvent is filled and dried in the groove 13 (the channel). More specifically, a solution of an above surfactant diluted with an alcohol such as isopropyl alcohol (IPA) is fed into the groove 13 (the channel) from the introduction unit 120, and the solution covers the entire groove 13. The solution is then dried. With this, the hydrophilic film 14 made from a surfactant can be formed on the surfaces of the groove 13.

In this way, forming the hydrophilic film 14 on the inner surfaces of the groove 13 gives the inner wall surfaces of the channel 100 a hydrophilic surface.

Figure 8:
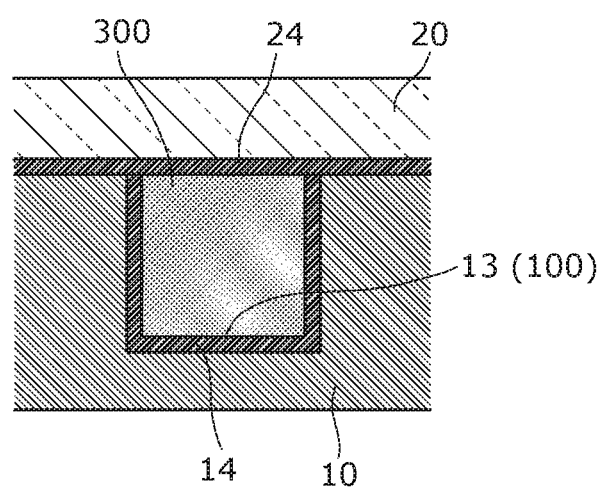
FIG. 8 is a cross sectional view of another example of a channel of a nucleic acid amplification device according to Embodiment 1 of the present invention.

Note that only a portion of the wall surfaces of the channel 100 is required have a hydrophilic surface, but wall surfaces around the entire perimeter of the channel 100 in a cross section taken perpendicular to the feeding direction are preferably hydrophilic surfaces. In this case, instead of forming the hydrophilic film 14 on the surfaces of the groove 13 of the first substrate 10, a hydrophilic film 24 may be formed on the second substrate 20 to give the surface of the second substrate 20 (the inner surface) a hydrophilic film surface, as illustrated in FIG. 8. The hydrophilic film 24 can be formed with the same material and by the same method as the hydrophilic film 14.

Moreover, the material for the hydrophilic film 14 is not limited to a surfactant; the material may be silicon oxide ($SiO_2$). In this case, the hydrophilic film 14 (silicon oxide film) can be formed using the method illustrated in FIG. 9. FIG. 9 illustrates cross sectional views of the nucleic acid amplification device according to Embodiment 1 of the present invention to illustrate the flow of the manufacturing method of the nucleic acid amplification device.

As illustrated in (a) in FIG. 9, for example, a 525 μm thick silicon substrate (for example, a silicon wafer) is prepared as the first substrate 10, and, for example, a 650 nm thick silicon oxide film 15 is formed on the entire surface of the silicon substrate as a thermally-oxidized film to be used as a hard mask in a subsequent etching process.

Next, as illustrated in (b) in FIG. 9, the silicon oxide film 15 is patterned into a predetermined shape by photolithography and etching. More specifically, the regions of the silicon oxide film 15 to become the groove 13 (the channel 100) are selectively removed, thereby exposing the first substrate 10.

Next, as illustrated in (c) in FIG. 9, the exposed portion of the first substrate 10 is etched using the patterned silicon oxide film 15 as a hard mask, whereby the groove 13 of a predetermined depth is formed.

Here, when the groove 13 is to have a rectangular or semicircular cross section, the groove 13 can be formed using a deep reactive ion etching (DRIE) process. Moreover, when the groove 13 is to have an inverted triangle cross section, the groove 13 can be formed with an anisotropic etching process using tetra methyl ammonium hydroxide (TMAH).

Next, after removing the hard mask of the silicon oxide film 15 by wet etching using hydrofluoric acid (in other words, after removing all of the silicon oxide film from the surface of the first substrate 10), in order to make the surfaces of the groove 13 (the channel 100) hydrophilic, a silicon oxide film that is approximately a 100 nm thermally-oxidized film is formed on the exposed surface of the first substrate 10 as the hydrophilic film 14, as illustrated in (d) in FIG. 9.

Lastly, as illustrated in (e) in FIG. 9, the second substrate 20, which includes the first through-hole 21 and the second through-hole 22, is joined with the first substrate 10. This forms the channel 100 having a configuration in which the opening of the groove 13 is sealed by the second substrate 20.

In this way, forming the hydrophilic film 14, which has a hydrophilic surface, on the inner surfaces of the groove 13 makes the inner wall surfaces of the channel 100 hydrophilic. With this, since self-propelled flow of the reaction solution 300 in the channel 100 is achieved by capillary forces acting at the air-water interface, the reaction solution 300 automatically advances through the channel 100. In other words, the reaction solution 300 is subjected to cyclic temperature change in the nucleic acid amplification reaction section 110 as the reaction solution 300 is fed through the channel 100 by automated transport.

More specifically, the reaction solution introduced into the introduction unit 120 automatically advances through the introduction channel 100c and enters the nucleic acid amplification reaction section 110, and in the nucleic acid amplification reaction section 110 automatically advances through the main channels 100a and sub channels 100b thereby passing back and forth through the high temperature zone and the low temperature zone, and then automatically advances through the discharge channel 100d and enters the discharge unit 130.

Note that the greater the percentage of the wall surface in the cross section of the channel 100 is hydrophilic, the greater the capillary force applied to the reaction solution.

Next, preferred channel size, solution viscosity, and capillary force with regard to the channel 100 of the nucleic acid amplification device 1 according to the present embodiment will be described in detail.

First, the theory behind using capillary force to feed liquid in the channel 100 will be described.

Feeding liquid using capillary force is determined by the balance between capillary force, which is the driving force, and pressure loss, which is the resistance component. Here, pressure loss $P_d$ can be represented as illustrated in (Expression 1) below.

[Math 1]

$$P_d = \frac{128 Q \eta l}{\pi D_h^4} \qquad \text{(Expression 1)}$$

In (Expression 1), Q represents amount of flow, $\eta$ represents viscosity of the solution, and l represents channel length. Moreover, in (Expression 1), $D_h$ is the hydraulic diameter defined by (Expression 2) below, and is a parameter that reflects the size and shape of the channel.

[Math 2]

$$D_d = \frac{4S}{U} \qquad \text{(Expression 2)}$$

In (Expression 2), S represents channel cross-sectional area, and U represents outer circumference length of the channel cross section.

(Expression 1) can be rewritten as (Expression 3) below by using feed velocity v and channel cross-sectional area S, and further inserting pressure loss coefficient $\alpha$.

[Math 3]

$$P_d = \frac{128 S v \eta l}{\pi D_h^4} = \alpha \times l \times v \qquad \text{(Expression 3)}$$

(Expression 3) illustrates that pressure loss $P_d$ is proportionate to channel length l and feed velocity v when a solution is fed through the channel.

Here, from the balance between pressure loss $P_d$ in (Expression 3) and capillary force $P_c$ ($P_d = P_c$), feed velocity v achieved by capillary force $P_c$ can be represented by (Expression 4) below.

[Math 4]

$$v = \frac{P_c}{\alpha} \times \frac{1}{l} \qquad \text{(Expression 4)}$$

In (Expression 4), $P_c/\alpha$ is a constant determined by the size and shape of the channel and the type of solution used, and here is defined as the feed coefficient and is used as an indicator of capillary force feeding characteristics.

The feed velocity v achieved by capillary force $P_c$ is a proportionality constant of the feed coefficient, and is inversely proportional to channel length l, that is to say, to the feed distance.

Moreover, since (Expression 4) is a differential equation of time t and feed distance (channel length l), by solving (Expression 4), feed distance l relative to time t is expressed as shown in (Expression 5) below, and is proportional to the square root of time t.

[Math 5]

$$l = \sqrt{2 \frac{P_c}{\alpha} t} \qquad \text{(Expression 5)}$$

In (Expression 5), which determines the feeding characteristics, pressure loss coefficient $\alpha$ is a significantly meaningful parameter.

Next, capillary force $P_c$ will be described in detail. Capillary force $P_c$ can be represented as a sum of the interfacial tensions of each side in the channel cross section, and can be expressed as (Expression 6) below.

[Math 6]

$$P_c = \frac{\sigma}{S} \sum_n \alpha_n \cos\theta_n \qquad \text{(Expression 6)}$$

In (Expression 6), $\sigma$ represents surface tension of the solution, S represents channel cross-sectional area, and $\alpha_n$ and $\theta_n$ represent the length of the sides in the channel cross section and contact angle, respectively. For example, when the channel has a rectangular cross section, capillary force $P_c$ is expressed as shown in (Expression 7).

[Math 7]

$$P_c = \sigma \left( \frac{\cos\theta_l + \cos\theta_r}{w} + \frac{\cos\theta_t + \cos\theta_b}{d} \right) \qquad \text{(Expression 7)}$$

Here, w and d represent the width and the depth of the channel, respectively, and $\theta_l$, $\theta_r$, $\theta_t$, and $\theta_b$, represent the contact angle of the left wall surface (left surface) of the channel, the contact angle of the right wall surface (right surface) of the channel, the contact angle of the top wall surface (top surface) of the channel, and the contact angle of the bottom wall surface (bottom surface) of the channel, respectively.

As is the case with the nucleic acid amplification device 1 according to the present embodiment, when the channel is designed for PCR by flow, the reaction solution continuously flows through regions of different temperature and shape. Therefore, there is a need to construct a theory regarding feeding that can accommodate any given temperature and shape.

Suppose a solution (liquid) is fed through a given channel by capillary force $P_c$, and the fluid front is at point x=l. Since capillary force $P_c$ is only associated with the fluid front of the fed solution, capillary force $P_c$ is represented by (Expression 6), and x=l is determined by the shape and temperature of the channel.

On the other hand, since pressure loss $P_d$ is associated with the entire region from point x=0 to point x=l, (Expression 3) needs to be expanded and considered as (Expression 8) below. In (Expression 8), pressure loss coefficient $\alpha$ is a constant determined by the temperature and shape at a given point x.

[Math 8]

$$P_d = \int_0^l \alpha dx \times v \quad \text{(Expression 8)}$$

Here, one can consider feed velocity v in a channel designed for PCR by flow to be determined by (Expression 9) below from the balance between pressure loss $P_d$ in (Expression 8) and capillary force $P_c$ ($P_d = P_c$).

[Math 9]

$$v = \frac{P_c}{\int_0^l \alpha dx} \quad \text{(Expression 9)}$$

(Expression 9) is the same as (Expression 4) except for the fact that the denominator to the right is an integral.

As shown above, in order to solve for feeding velocity v (flow speed) with (Equation 9), the dependency of capillary $P_c$ and pressure loss coefficient $\alpha$ on shape and temperature is large.

First, shape dependency and the temperature dependency of pressure loss coefficient $\alpha$ will be considered.

Pressure loss $P_d$ can be represented as illustrated in (Expression 3) above, and pressure loss coefficient $\alpha$ can be represented as illustrated in (Expression 10) below.

[Math 10]

$$\alpha = \frac{128 S \eta}{\pi D_h^4} \propto \frac{S \eta}{D_h^4} \quad \text{(Expression 10)}$$

Since the shape factor stems from S and $D_h$, pressure loss coefficient $\alpha$ clearly depends on shape.

However, the temperature dependency of pressure loss coefficient $\alpha$ is the temperature dependency of viscosity $\eta$ in (Expression 10), and the surface tension and contact angle are key parameters, but up until now, the temperature dependency of the viscosity characteristic of the PCR reagent has remained unknown.

In light of this, the Inventors of the present invention evaluated, in practice, pressure loss in a channel having a rectangular cross section with a width of 100 μm and a depth of 50 μm, and successfully observed the temperature dependency of the viscosity characteristic that strongly contributes to pressure loss. Moreover, the Inventors of the present invention focused on the feed coefficient $P_c/\alpha$, and obtained the capillary force by observing the feed coefficient. More specifically, the feed coefficient of the PCR reagent was observed at 25° C., 60° C., and 95° C. The capillary force was obtained from this feed coefficient and the viscosity characteristic obtained above. Hereinafter, the experiment conducted to obtain the feed coefficient and viscosity characteristics will be described.

Using this data, (Expression 6), and (Expression 10), the feeding characteristics in a given channel can be designed.

First, since an experiment regarding the capillary force feeding characteristics in the channel was performed, that experiment will be described.

In this experiment, in order to obtain the viscosity characteristics and capillary force of the PCR reagent at 60° C. and ° C., the feeding by capillary force (in other words, the displacement of the fluid front in the microchannel in relation to time and pressure loss) was measured. Note that the channel 100 in the nucleic acid amplification device 1 has a width of 100 μm and a depth of 50 μm, and 25° C. deionized water (DW) and 25° C., 60° C., and 95° C. PCR reagent was used.

Figure 10:
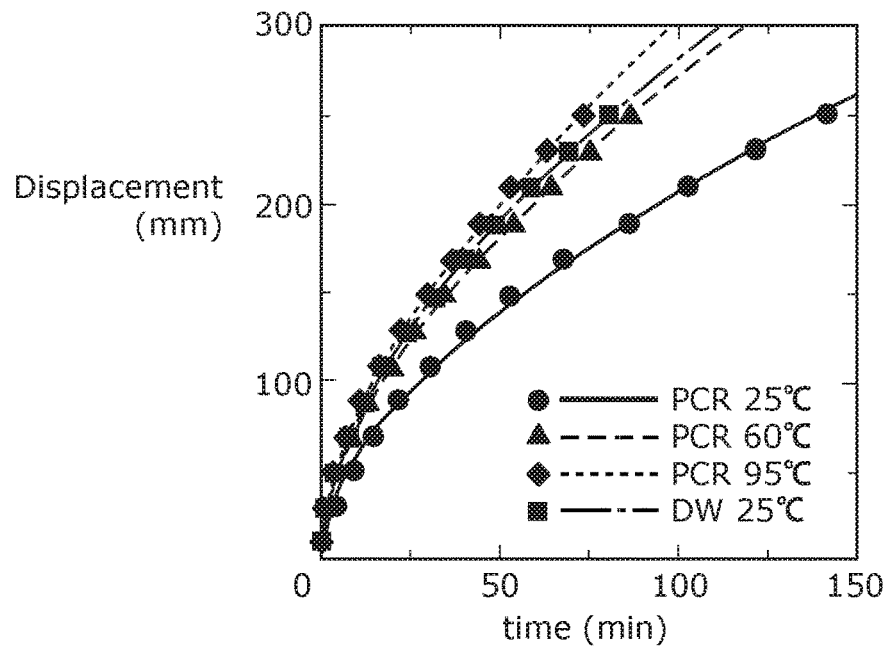
FIG. 10 illustrates the relationship between time and fluid front displacement of 25° C., 60° C., and 95° C. PCR reagent and 25° C. deionized water.

The results of the experiment are illustrated in FIG. 10. FIG. 10 illustrates the relationship between time and fluid front displacement of 25° C., 60° C., and 95° C. PCR reagent and 25° C. deionized water. The results of this experiment show that a constant approximate curve relating to capillary force (capillary force feeding characteristics) can be obtained depending on the temperature of the reaction solution.

Next, since an experiment regarding evaluation of pressure loss in the channel was performed, that experiment will be described.

Figure 11:
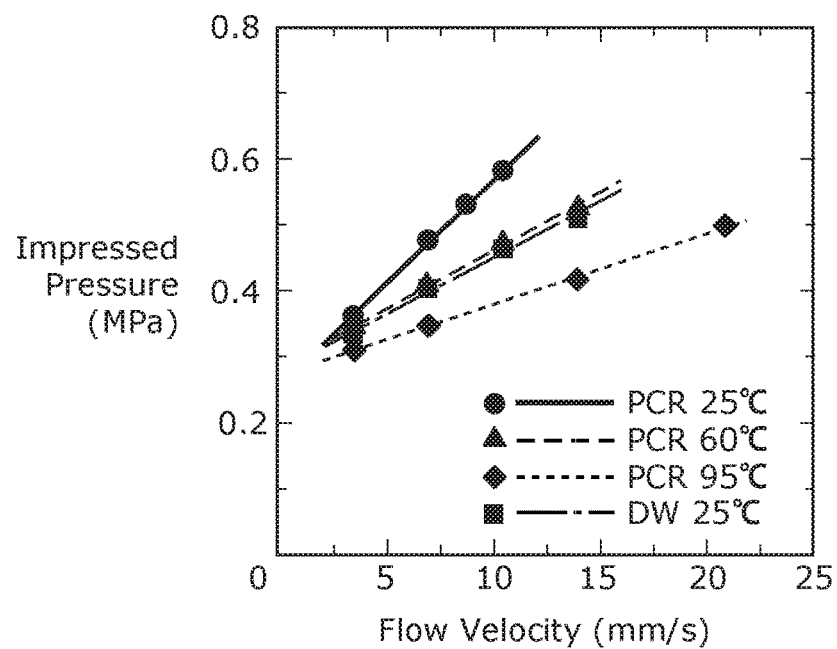
FIG. 11 illustrates the results of pressure loss observed in 25° C., 60° C., and 95° C. PCR reagent and 25° C. deionized water.

When feeding by capillary force, pressure loss by the channel is one of the main factors determining feeding velocity. FIG. 11 illustrates the results of pressure loss observed in 25° C., 60° C., and 95° C. PCR reagent and 25° C. deionized water. Note that the pressure loss value was calculated based load cell power and a cross-sectional area of the syringe. All pressure loss is proportional to feeding velocity such as shown in (Expression 1).

As illustrated in FIG. 11, the viscosity of the PCR reagent can be calculated based on the ratio of pressure to feeding velocity (pressure/feeding velocity).

In light of these experimentation results, viscosity and capillary force can be obtained from the capillary force feeding characteristics (approximate curve) illustrated in FIG. 10 and pressure loss. With this, it is possible to predict feeding performed during nucleic acid amplification.

Figures 12, 13:
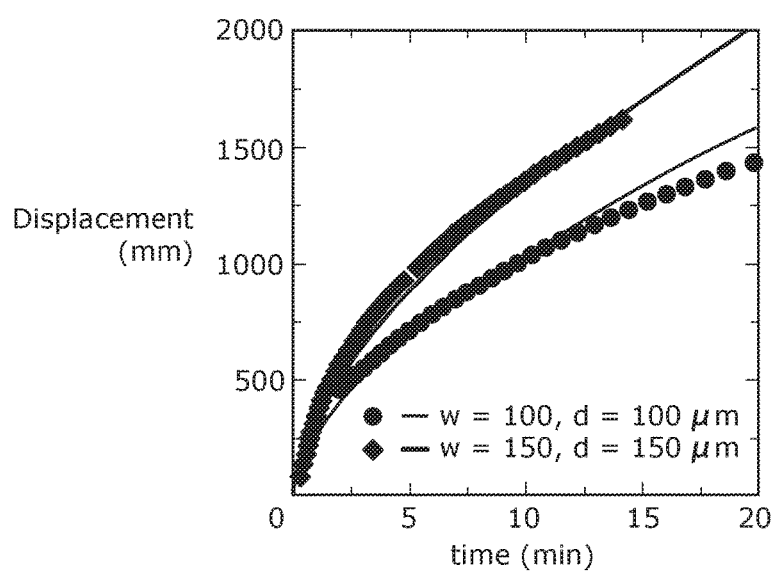
FIG. 12 illustrates calculated viscosity and capillary force values for 25° C., 60° C., and 95° C. PCR reagent and 25° C. deionized water.
FIG. 13 illustrates the relationship between time and fluid front displacement of the self-propelled flow of the PCR reagent through the channel by capillary force.

The viscosity (viscosity characteristics) and capillary force for 25° C., 60° C., and 95° C. PCR reagent and 25° C. deionized water were calculated with the above experimentation, as illustrated in FIG. 12. Here, since it is widely known that the viscosity of 25° C. deionized water is q=0.00089 Pa·s, the fact that the viscosity of the 25° C. deionized water in this experiment was η=0.00099 Pa·s confirms the validity of this experiment. Moreover, it is widely known that the surface tension of 25° C. deionized water is σ=0.073 N/m. Since the capillary force of 25° C. deionized water calculated from this value is 4.3 kPa, the fact that the capillary force of the 25° C. deionized water in this experiment was 4.4 kPa also confirms the validity of this experiment.

Next, since an experiment regarding nucleic acid amplification using a PCR reagent as the reagent was performed, the results of that experiment will be described.

In this experiment, the above-described nucleic acid amplification device 1 was used as the microfluidic device. Here, as illustrated in FIG. 7A through FIG. 7C, the contact angle θ of the 25° C. deionized water on the hydrophilic film (silicon oxide film) 14 formed in the groove 13 and on the surface of the second substrate 20, which is a glass substrate, was 49° in either case. Moreover, the temperature of the first heater block 141 was 95° C., the temperature of the second heater block 142 was 60° C., and the reaction solution flowing through the channel 100 cyclically passed through two temperature zones of 95° C. and 60° C. alternately.

The capillary force feeding characteristics when the size of the channel 100 was changed for the experiment illustrated in FIG. 10 will be described using FIG. 13. FIG. 13 illustrates the relationship between time and fluid front displacement of the self-propelled flow of the PCR reagent through the channel by capillary force. Note that in FIG. 13, results are shown for when the channel is a rectangle having a width W of 100 μm and a depth d of 100 μm, and for when the channel is a rectangle having a width W of 150 μm and a depth d of 150 μm.

In this way, by changing the size of the channel 100, it can be seen that desired capillary force feeding characteristics can be obtained.

Next, nucleic acid amplification when human genome β-actin, complementary DNA generated from influenza virus AH1pdm RNA, and *Escherichia coli* genome DNA 16SrDNA are used as the PCR reagent will be described.

Figure 14:
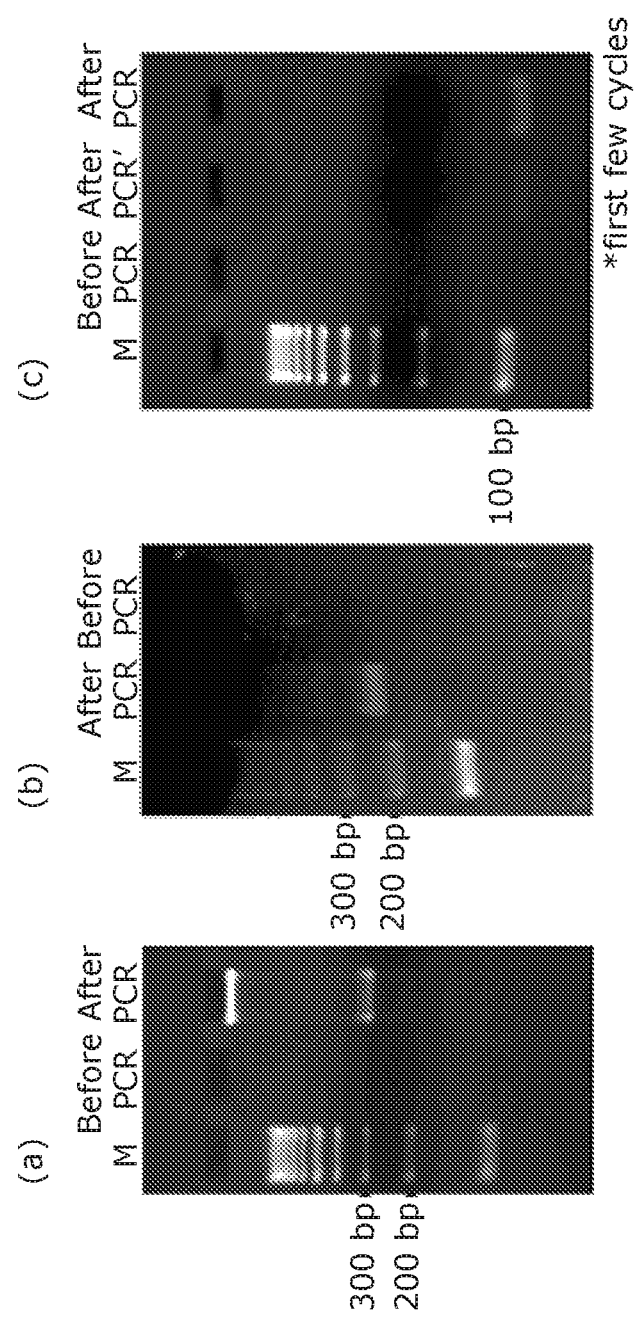
FIG. 14 illustrates in (a)-(c) gel electrophoresis images of standard DNA markers before and after PCR amplification.

The results of when nucleic acid amplification was performed using these PCR reagents which flow in a self-propelled manner by capillary force are illustrated in FIG. 14. FIG. 14 illustrates gel electrophoresis images of standard DNA markers before and after PCR amplification and, more specifically, (a) illustrates human genome β-actin, (b) illustrates influenza virus AH1pdm, and (c) illustrates *Escherichia coli* genome DNA 16SrDNA.

As illustrated in FIG. 14, the amplification of human genome β-actin was 295 bp, the amplification of influenza virus AH1pdm was 232 bp, and the amplification of *Escherichia coli* genome DNA 16SrDNA was 95 bp.

In this way, with the nucleic acid amplification device 1 according to the present embodiment, it is possible to perform nucleic acid amplification of a target nucleic acid by feeding the reaction solution including the target nucleic acid by capillary force.

[Nucleic Acid Amplification Apparatus]

Figure 15:
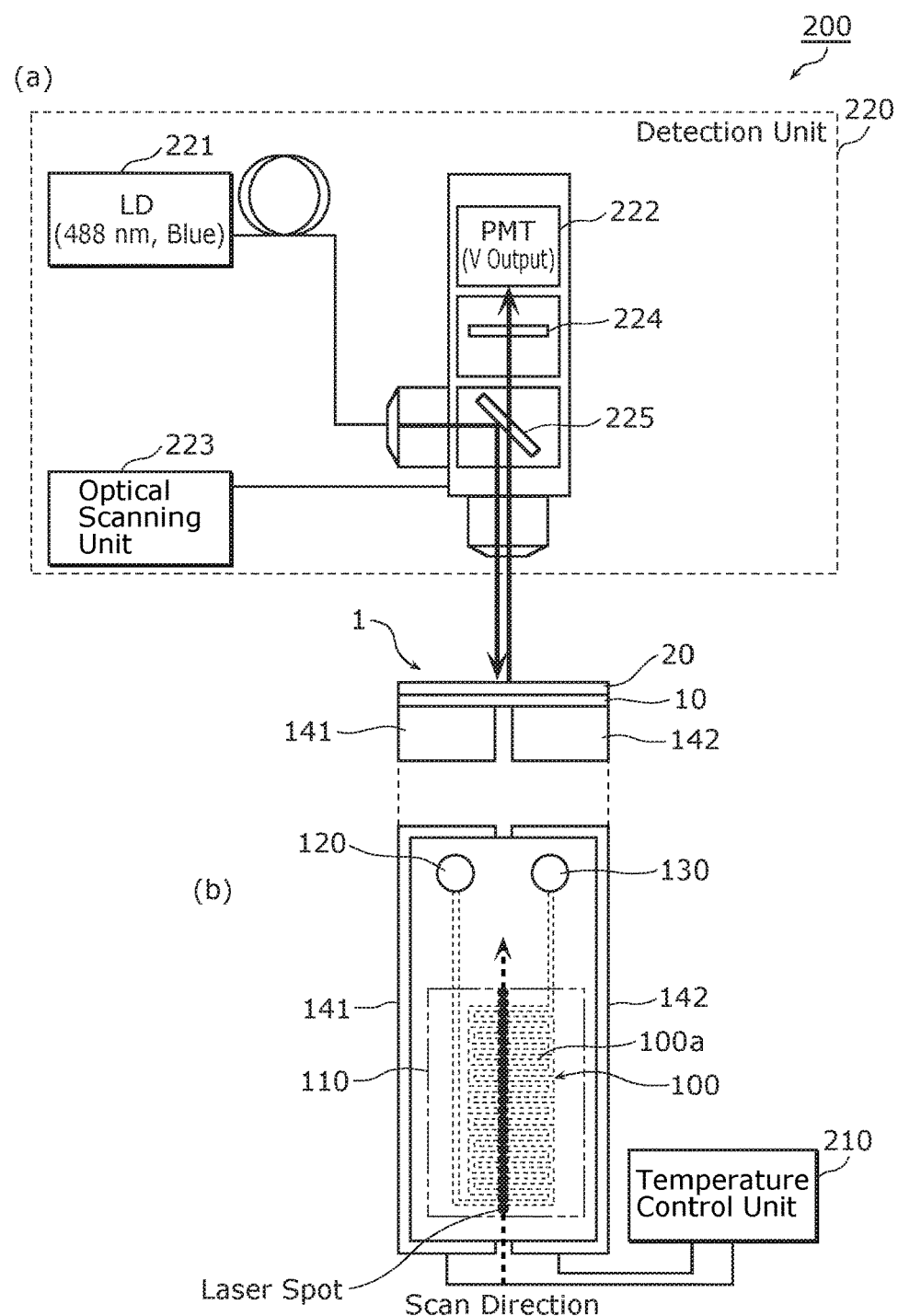
FIG. 15 illustrates in (a) and (b) the configuration of a nucleic acid amplification apparatus according to Embodiment 1 of the present invention.

First, the configuration of a nucleic acid amplification apparatus 200 according to Embodiment 1 of the present invention will be described using FIG. 3 and FIG. 15. FIG. 15 illustrates the configuration of a nucleic acid amplification apparatus according to Embodiment 1 of the present invention.

As illustrated in FIG. 3, the nucleic acid amplification apparatus 200 according to the present embodiment includes the above-described nucleic acid amplification device 1 and the temperature control unit 210 for controlling the temperature of the nucleic acid amplification reaction section 110 in the nucleic acid amplification device 1. With this configuration, nucleic acid amplification is possible with a simple method.

As illustrated in (a) in FIG. 15, the nucleic acid amplification apparatus 200 according to the present embodiment further includes a detection unit 220 for detecting nucleic acid amplification of the target nucleic acid.

The detection unit 220 is an optical detection system, and includes a light output unit 221 that outputs light for irradiating the nucleic acid amplification device 1, a light receptor unit 222 that receives reflected light of the light irradiating the nucleic acid amplification device 1 and an optical scanning unit 223 for scanning the light over the channel 100 of the nucleic acid amplification device 1.

The light output unit 221 includes a laser element that emits blue light, and outputs, for example, laser light having a central wavelength of 488 nm. The light receptor unit 222 is, for example, a photomultiplier tube (PMT). Note that the detection unit 220 also includes other optical elements such as an excitation cut filter 224 and a dichroic mirror 225.

In this way, the nucleic acid amplification apparatus 200 according to the present embodiment is an integrated evaluation system configured of a heating-and-cooling system (the temperature control unit 210) and an optical detection system (the detection unit 220). Integrating in a detection system in this way allows for a simple detection apparatus to be realized. Moreover, integrating the optical detection system makes it possible to detect the amount of amplification of the nucleic acid in a contactless manner.

When detecting the amount of amplification of the target nucleic acid in the reaction solution (the reaction sample, the reagent) introduced into the nucleic acid amplification device 1, laser light is scanned in a direction intersecting the main channels 100a of the channel 100 and the reflected light is received, as illustrated in (b) in FIG. 15. The amplification amount of the target nucleic acid in the reaction solution in the channel 100 is calculated based on the received reflected light. This makes it possible to obtain a nucleic acid amplification curve corresponding to the cycle of the channel 100 that passes back and forth through the first heater block 141 and the second heater block 142.

In the present embodiment, by irradiating the reaction solution with blue laser light, the blue light acts as excitation light, and green light emitted by fluorescence reflects back as reflected light. The fluorescence of this green light (reflected light) varies depending on the amplification amount of the nucleic acid. As such, the amplification amount of the nucleic acid can be calculated by measuring the fluorescence of the green light.

Figure 16:
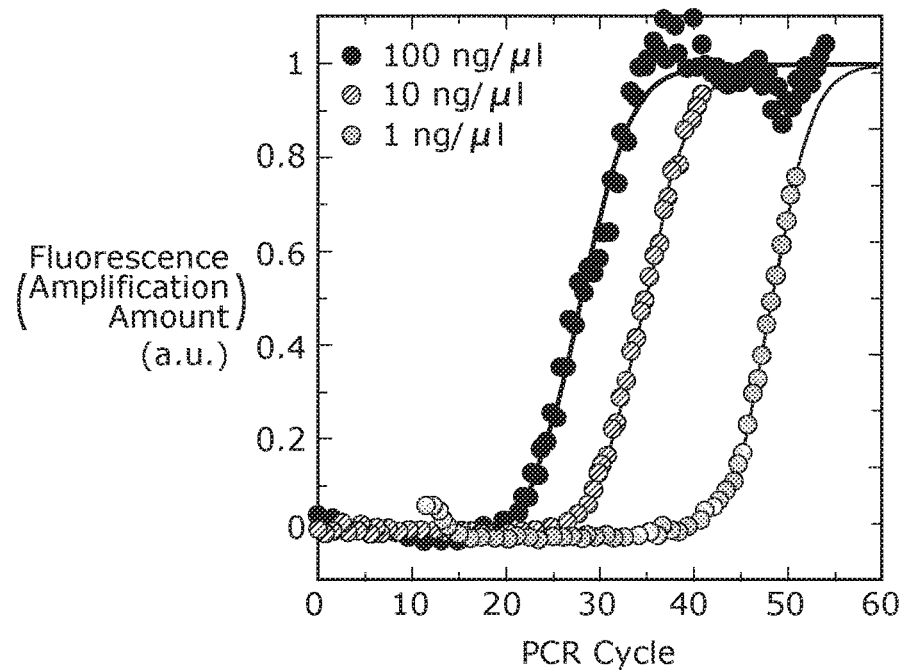
FIG. 16 illustrates the relationship between the PCR cycle of the reaction solution and fluorescence (amplification amount).
Figure 17:
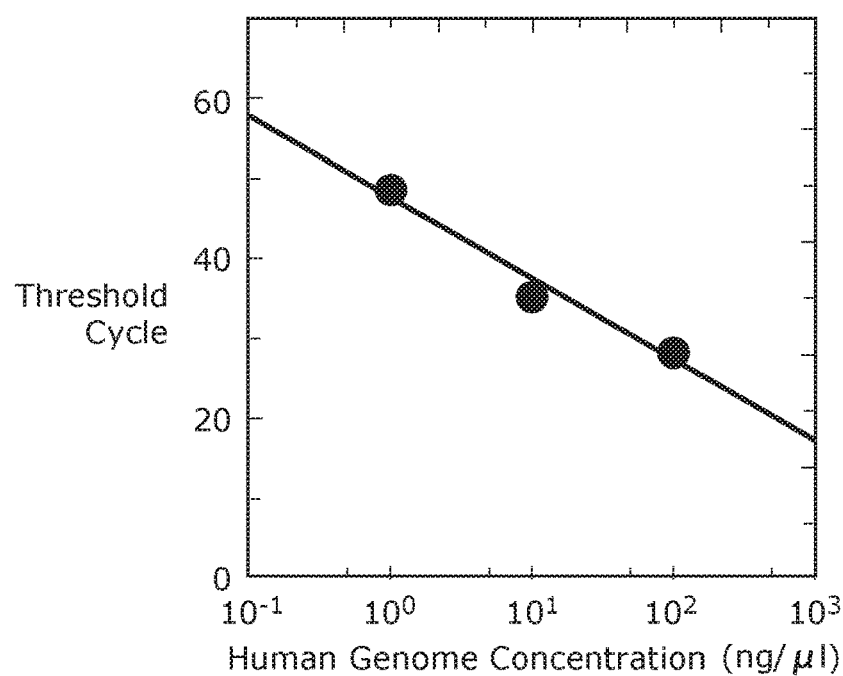
FIG. 17 illustrates the relationship between reaction sample (human genome) concentration and the threshold cycle at start up.

Here, one example of optical detection results when a reaction solution including human genome β-actin as the reaction sample was used will be described using FIG. 16 and FIG. 17. FIG. 16 illustrates the relationship between the PCR cycle of the reaction solution and fluorescence (amplification amount). FIG. 17 illustrates the relationship between reaction sample (human genome) concentration and the threshold cycle at start up.

As illustrated in (a) and (b) in FIG. 15, the amplification amount of the nucleic acid per cycle of the channel 100 (per main channel 100a) can be detected as an amplification curve by scanning laser light across the channel 100.

The result, as illustrated in FIG. 16, shows that the amplification amount of the nucleic acid increases as the number of PCR cycles increases. The result also shows that the threshold cycle at start up changes depending on the initial concentration of the reaction sample (human genome). Thus, by defining the threshold cycle at start up as a cycle having a maximum value (saturation value) of approximately 10%, for example, a significantly linear calibration curve can be obtained, as illustrated in FIG. 17, and an initial concentration can be determined.

Embodiment 2

Next, the configuration of a nucleic acid amplification device 2 according to Embodiment 2 of the present invention will be described using FIG. 18A and FIG. 18B. FIG. 1.8A is a plan view of the nucleic acid amplification device according to Embodiment 2 of the present invention, and FIG. 18B is an enlarged plan view of the mixing unit in the same nucleic acid amplification device.

Figure 18A:
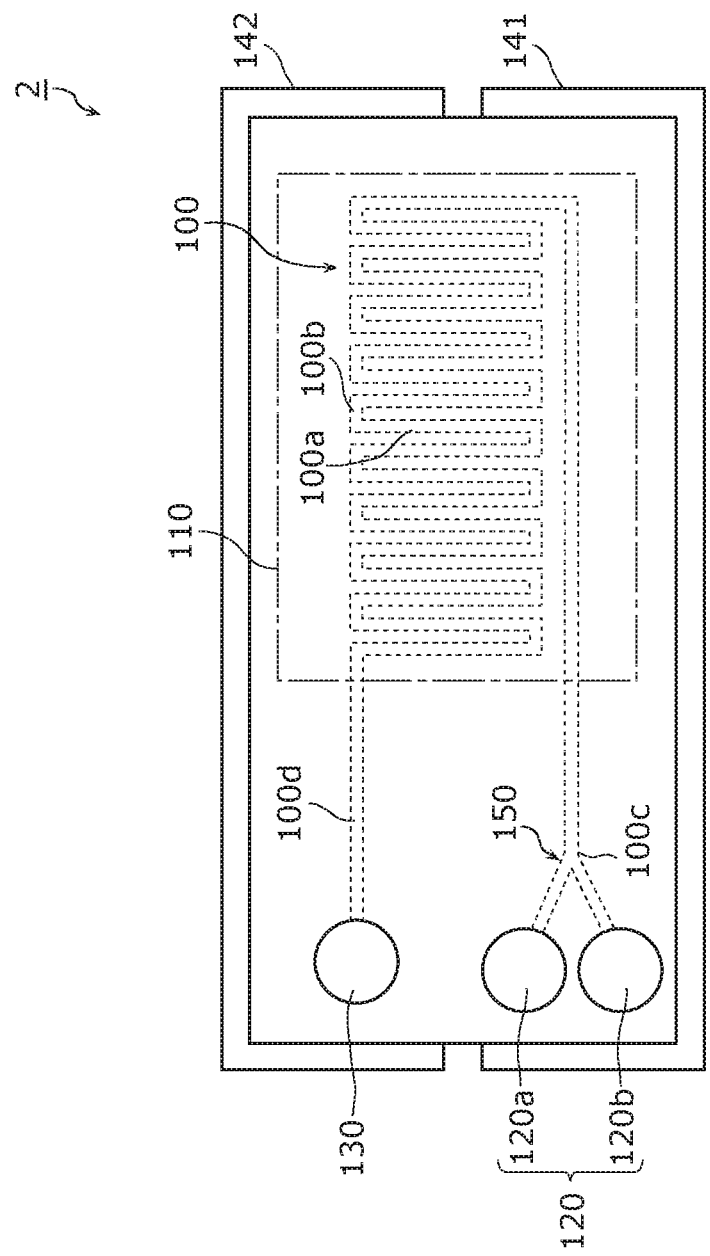
FIG. 18A is a plan view of a nucleic acid amplification device according to Embodiment 2 of the present invention.
Figure 18B:
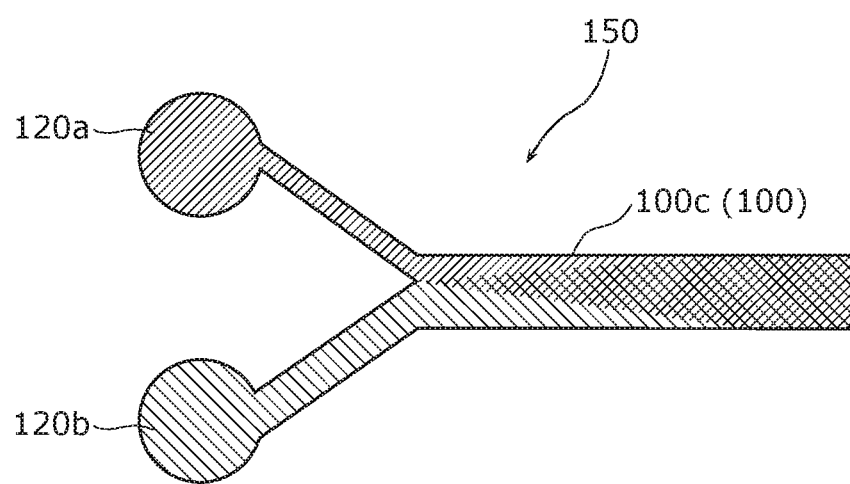
FIG. 18B is an enlarged plan view of a mixing unit in a nucleic acid amplification device according to Embodiment 2 of the present invention.

As illustrated in FIG. 18A and FIG. 18B, the nucleic acid amplification device 2 according to the present embodiment includes a plurality of the introduction units 120 of the nucleic acid amplification device 1 according to Embodiment 1.

More specifically, the nucleic acid amplification device 2 includes a first introduction unit 120a and a second introduction unit 120b, and further includes a mixing unit 150 disposed between (i) the first introduction unit 120a and the second introduction unit 120b and (ii) the nucleic acid amplification reaction section 110.

The introduction channel 100c according to the present embodiment is formed in a Y-shape such that the first introduction unit 120a and the second introduction unit 120b are branches. The first introduction unit 120a and the second introduction unit 120b are connected as one in the mixing unit 150 via the introduction channels 100c that correspond to the first introduction unit 120a and the second introduction unit 120b.

In this way, the mixing unit 150 is a portion of the introduction channel 100c, and in the mixing unit 150, the plurality of solutions introduced from the first introduction unit 120a and the second introduction unit 120b are mixed together. In other words, the mixing unit 150 is where a first solution introduced into the first introduction unit 120a and a second solution introduced into the second introduction unit 120b are mixed together.

Note that a solution including a target nucleic acid, for example, is introduced into the first introduction unit 120a as the first solution. Moreover, a solution including a reagent, for example, is introduced into the second introduction unit 120b as the second solution.

As illustrated in FIG. 18B, in the present embodiment, the first solution introduced into the first introduction unit 120a and the second solution introduced into the second introduction unit 120b are mixed together by diffusion in the mixing unit 150. This makes it possible to achieve a mixture with a simple configuration.

Figure 19:
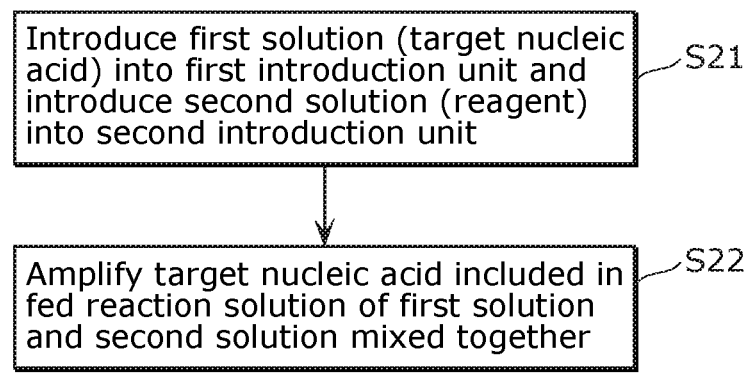
FIG. 19 is a flow chart of a nucleic acid amplification method according to Embodiment 2 of the present invention.

Next, the nucleic acid amplification method according to Embodiment 2 of the present invention will be described using FIG. 19. FIG. 19 is a flow chart of the nucleic acid amplification method according to Embodiment 2 of the present invention.

The nucleic acid amplification method according to the present embodiment is a method for amplifying a target nucleic acid using the above-described nucleic acid amplification device 2, and includes: introducing the target nucleic acid sample and a reagent for amplifying the target nucleic acid into the introduction unit 120 of the nucleic acid amplification device 2; and as the reaction solution including the target nucleic acid and the reagent is fed by capillary force, amplifying the target nucleic acid included in a reaction solution.

In the present embodiment, in the above-described introducing, the solution including the target nucleic acid (the first solution) and the solution including the reagent (the second solution) are separately introduced into the nucleic acid amplification device 2, and in the amplifying, the solution including the target nucleic acid (the first solution) and the solution including the reagent (the second solution) mix together in the nucleic acid amplification device 2 to produce the reaction solution, and the target nucleic acid included in the reaction solution is amplified by subjecting the reaction solution to cyclic temperature changes as the reaction solution is fed by capillary force.

More specifically, as illustrated in FIG. 19, the solution including the target nucleic acid and the solution including the reagent are introduced at the same time into the first introduction unit 120a as the first solution and the second introduction unit 120b as the second solution, respectively (step S21).

The first solution and the second solution separately introduced into the first introduction unit 120a and the second introduction unit 120b pass through different introduction channels 100c and mix together in the mixing unit 150 to produce the reaction solution, which is fed to the nucleic acid amplification reaction section 110, and similar to Embodiment 1, the target nucleic acid included in the reaction solution is amplified by subjecting the reaction solution to cyclic temperature changes (step S22).

The reaction solution is subsequently fed from the nucleic acid amplification reaction section 110 to the discharge unit 130 via the discharge channel 100d, and discharged by the discharge unit 130.

With the nucleic acid amplification device 2 according to the present embodiment, since the reaction solution can be fed by capillary force similar to Embodiment 1, the reaction solution can be advanced in the channel without the use of an external pump. Consequently, nucleic acid amplification of the target nucleic acid can be performed at low cost and easily.

Furthermore, according to the present embodiment, the target nucleic acid and the reagent can be mixed in the device, which makes nucleic acid amplification or the target nucleic acid is even simpler to perform.

Variation 1 of Embodiment 2

Figure 20:
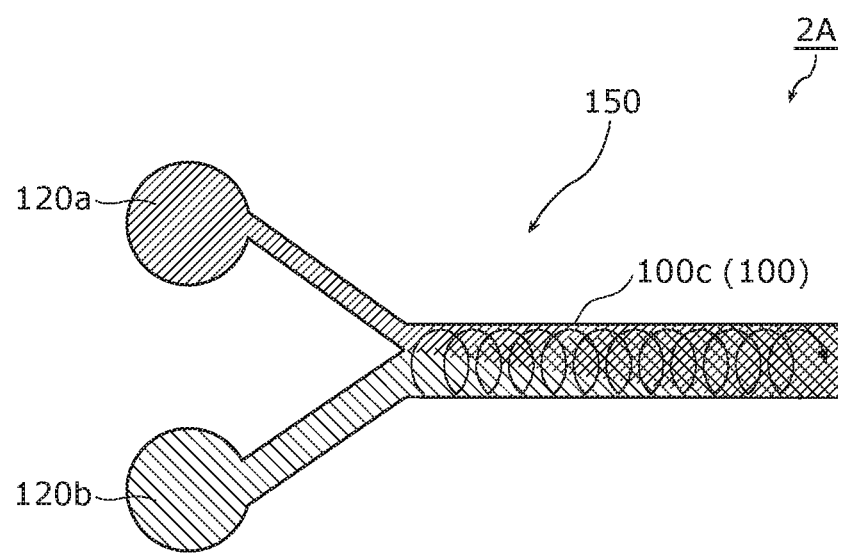
FIG. 20 is an enlarged plan view of a mixing unit in a nucleic acid amplification device according to Variation 1 of Embodiment 2 of the present invention.

Next, the configuration of a nucleic acid amplification device 2A according to Variation 1 of Embodiment 2 of the present invention will be described using FIG. 20. FIG. 20 is an enlarged plan view of the mixing unit in the nucleic acid amplification device according to Variation 1 of Embodiment 2 of the present invention.

As illustrated in FIG. 20, in the nucleic acid amplification device 2A according to the present variation, the first solution and the second solution introduced into the first introduction unit 120a and the second introduction unit 120b are mixed in the mixing unit 150 by helicoidal flow. For example, cutting cork-screw-like grooves in the inner walls of the channel 100 generates a helicoidal flow of the first solution and the second solution thereby mixing together the first solution and the second solution.

In this way, by generating a helicoidal flow in the mixing unit 150, mixing by agitation is possible, and a plurality of solutions can be evenly mixed in a rapid manner.

Variation 2 of Embodiment 2

Figure 21:
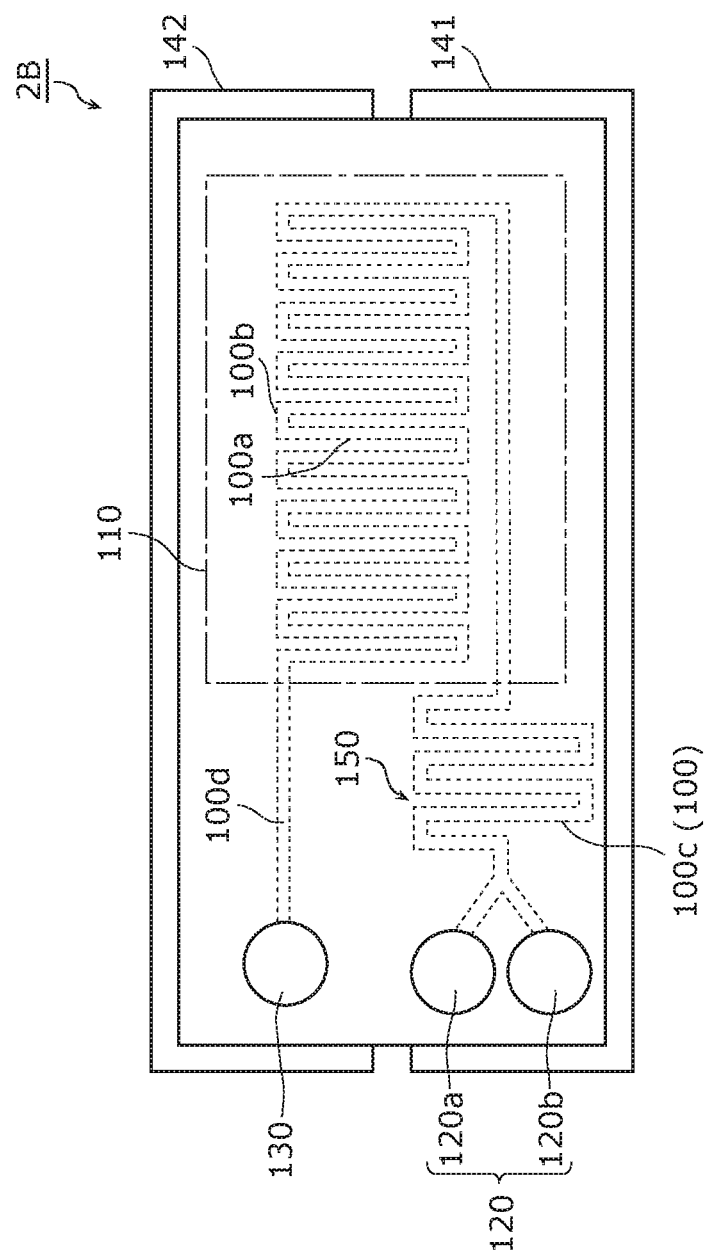
FIG. 21 is a plan view of a nucleic acid amplification device according to Variation 2 of Embodiment 2 of the present invention.

Next, the configuration of a nucleic acid amplification device 2B according to Variation 2 of Embodiment 2 of the present invention will be described using FIG. 21. FIG. 21 is a plan view of the nucleic acid amplification device according to Variation 2 of Embodiment 2 of the present invention.

As illustrated in FIG. 21, in the nucleic acid amplification device 2B according to the present variation, the portion of the channel 100 in the mixing unit 150 (the mixing unit channel) is a meandering channel.

With this configuration, since a distance necessary to diffuse and mix the plurality of solutions can be secured, even when the reaction solution is prepared by mixing the plurality of solutions in the device, it is possible to evenly mix the plurality of solutions before the reaction solution reaches the nucleic acid amplification reaction section 110.

Variation 3 of Embodiment 2

Figure 22:
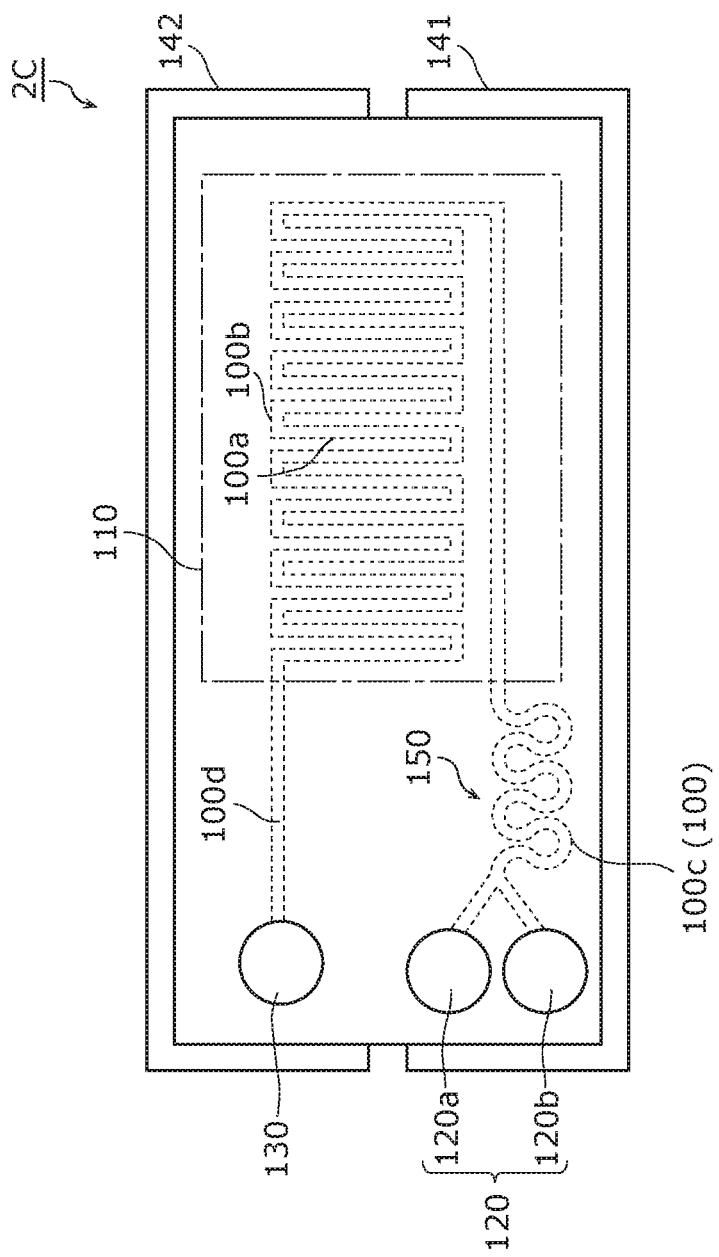
FIG. 22 is a plan view of a nucleic acid amplification device according to Variation 3 of Embodiment 2 of the present invention.

Next, the configuration of a nucleic acid amplification device 2C according to Variation 3 of Embodiment 2 of the present invention will be described using FIG. 22. FIG. 22 is a plan view of the nucleic acid amplification device according to Variation 3 of Embodiment 2 of the present invention.

As illustrated in FIG. 22, in the nucleic acid amplification device 2C according to the present variation, the portion of the channel 100 in the mixing unit 150 (the mixing unit channel) is a loop-shaped channel. More specifically, a plurality of C-shaped loop channels are alternately rotated 180 degrees and connected together.

With this configuration, since conical flow can be easily generated, a plurality of solutions can be evenly mixed together easily.

Variation 4 of Embodiment 2

Figure 23:
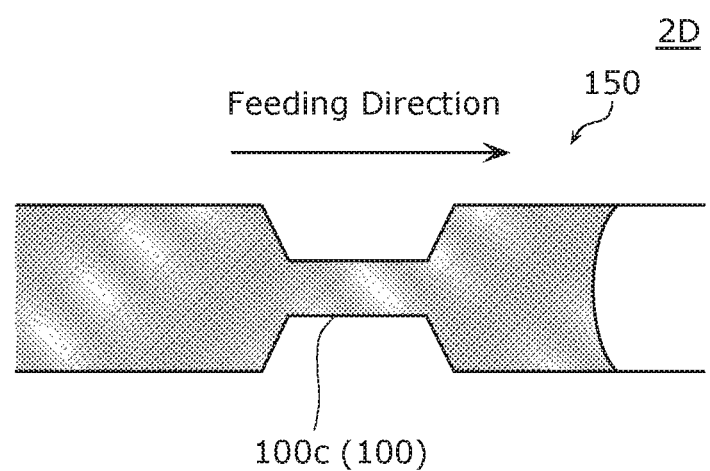
FIG. 23 is an enlarged plan view of a mixing unit in a nucleic acid amplification device according to Variation 4 of Embodiment 2 of the present invention.

Next, the configuration of a nucleic acid amplification device 2D according to Variation 4 of Embodiment 2 of the present invention will be described using FIG. 23. FIG. 23 is an enlarged plan view of the mixing unit in the nucleic acid amplification device according to Variation 4 of Embodiment 2 of the present invention.

As illustrated in FIG. 23, in the nucleic acid amplification device 2D according to the present variation, the portion of the channel 100 in the mixing unit 150 (the mixing unit channel) has a section having a cross-sectional area that sectionally decreases. For example, by narrowing the width of a portion of the channel in the mixing unit 150, the channel cross-sectional area can be made to sectionally decrease.

With this configuration, since the plurality of solutions can be mixed in a short period of time in an area having a small cross-sectional area, the distance over which the plurality of solutions are mixed can be decreased. With this, it is possible to achieve a compact nucleic acid amplification device.

Embodiment 3

Figure 24A:
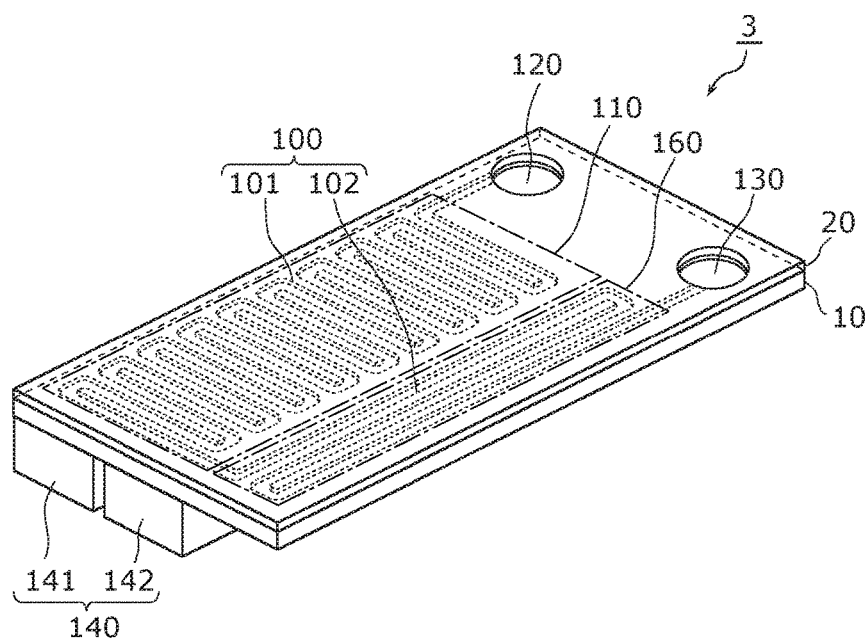
FIG. 24A is a perspective view of a nucleic acid amplification device according to Embodiment 3 of the present invention.
Figure 24B:
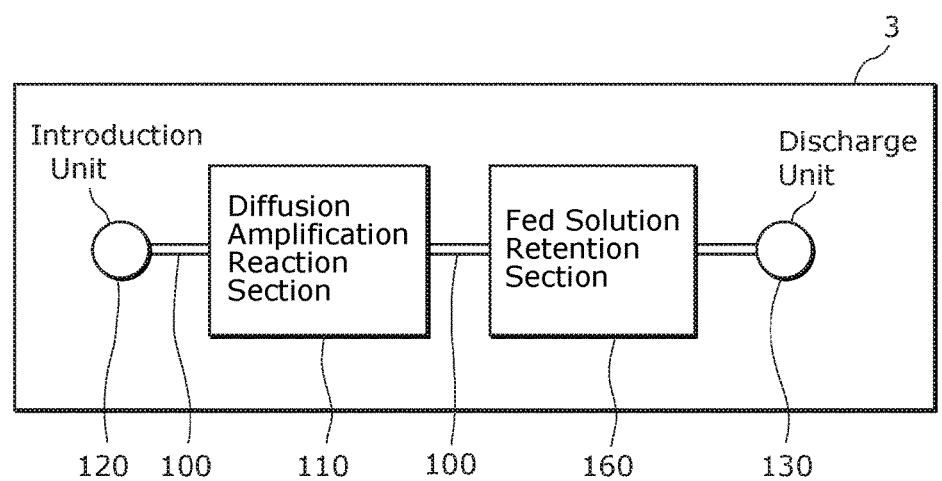
FIG. 24B is a schematic view of a nucleic acid amplification device according to Embodiment 3 of the present invention.
Figure 25:
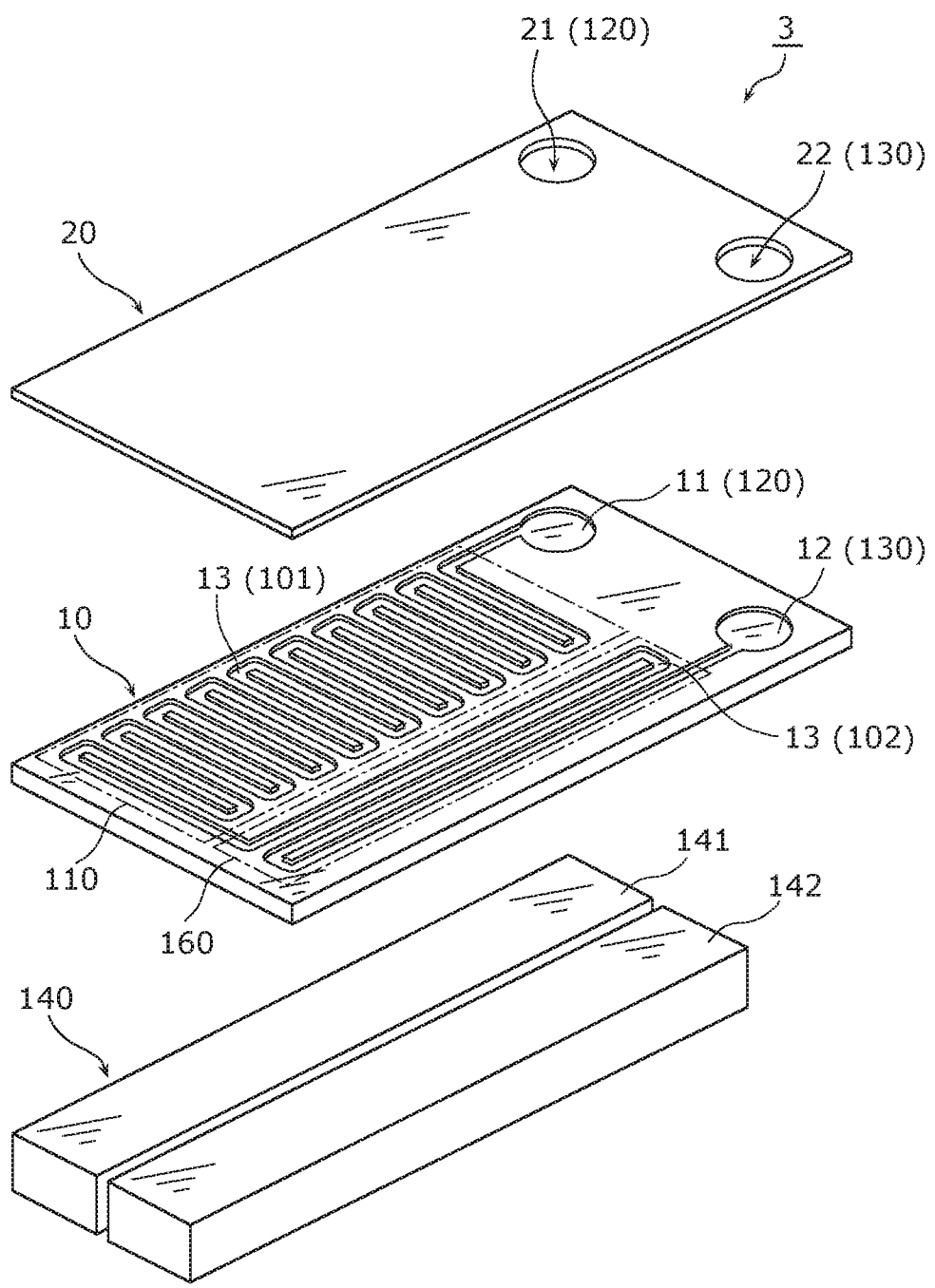
FIG. 25 is an exploded perspective view of a nucleic acid amplification device according to Embodiment 3 of the present invention.

Next, the configuration of a nucleic acid amplification device 3 according to Embodiment 3 of the present invention will be described using FIG. 24A, FIG. 24B and FIG. 25. FIG. 24A is a perspective view of the nucleic acid amplification device according to Embodiment 3 of the present invention, and FIG. 24B illustrates a schematic configuration of the same nucleic acid amplification device. FIG. 25 is an exploded perspective view of the same nucleic acid amplification device.

As illustrated in FIG. 24A through FIG. 25, the nucleic acid amplification device 3 according to the present embodiment has a configuration in which the nucleic acid amplification device 1 according to Embodiment 1 further includes a fed solution retention section 160.

The fed solution retention section 160 is a fed solution retention region for retaining the reaction solution. In other words, the fed solution retention section 160 is a fed solution advancement section for keeping the front portion of the reaction solution from stagnating in the nucleic acid amplification reaction section 110 and advancing the fluid front of the reaction solution ahead of the nucleic acid amplification reaction section 110. The fed solution retention section 160 is configured so that a given amount of the reaction solution can be retained therein. Note that the reaction solution retained in the fed solution retention section 160 may be stopped so as not to flow or may advanced so the flow does not stop.

The channel 100 in the present embodiment passes through the fed solution retention section (fed solution retention region) 160 in addition to the nucleic acid amplification reaction section. More specifically, the channel 100 includes a first channel 101 disposed in the nucleic acid amplification reaction section 110 and a second channel 102 disposed in the fed solution retention section 160.

As illustrated in FIG. 25, the portion of the channel 100 in the nucleic acid amplification reaction section 110 (the first channel 101) is a meandering channel formed so as to meander in such a manner as to alternately pass through the first heater block 141 (the first temperature zone) and the second heater block 142 (the second temperature zone) repeatedly.

The portion of the channel 100 in the fed solution retention section 160 (the second channel 102) is a channel for retaining the reaction solution in the fed solution retention section 160, and a channel that can retain a predetermined amount of the reaction solution including the front portion of the reaction solution fed into the fed solution retention section 160 (the second channel 102). Since the fed solution retention section 160 is provided downstream the nucleic acid amplification reaction section 110, the reaction solution fed from the first channel 101 (the nucleic acid amplification reaction section 110) is retained in the second channel 102.

In the present embodiment, the second channel 102 includes a meandering portion (meandering channel). More specifically, the second channel 102 is formed so as to continuously bend back on itself (run back and forth) at bends located at predetermined intervals in the line-shaped channel. The number of bend-backs in the second channel 102 and the directionality of the channel may be appropriately changed depending on the space available.

The volumetric capacity (cubic volume) of the second channel 102 is 10% or more of the total volumetric capacity (cubic volume) of the channel 100, and preferably 30% or more of the total volumetric capacity (cubic volume) of the channel 100. In the present embodiment, the volumetric capacity of the second channel 102 is approximately 30% of the total volumetric capacity of the channel 100.

As illustrated in FIG. 24A through FIG. 25, the heater unit 140 is disposed so as to at least oppose the nucleic acid amplification reaction section 110, and the reaction solution fed through the portion of the channel 100 in the nucleic acid amplification reaction section 110 (the first channel 100) is subjected to a predetermined temperature by the heater unit 140. Note that in the present embodiment, the fed solution retention section 160 (the second channel 102) is not opposed to the heater unit 140 and is not directly subjected to a temperature by the heater unit 140. In other words, the second channel 102 is disposed so as to not be positioned above the heater unit 140.

In the present embodiment as well, the reaction solution introduced into the channel 100 via the introduction unit 120 is fed through the channel 100 by capillary force. For example, similar to Embodiment 1, the reaction solution can be fed by capillary force by giving the inner surfaces of the channel 100 a hydrophilic surface with an acute contact angle.

[Nucleic Acid Amplification Method]

Figure 26:
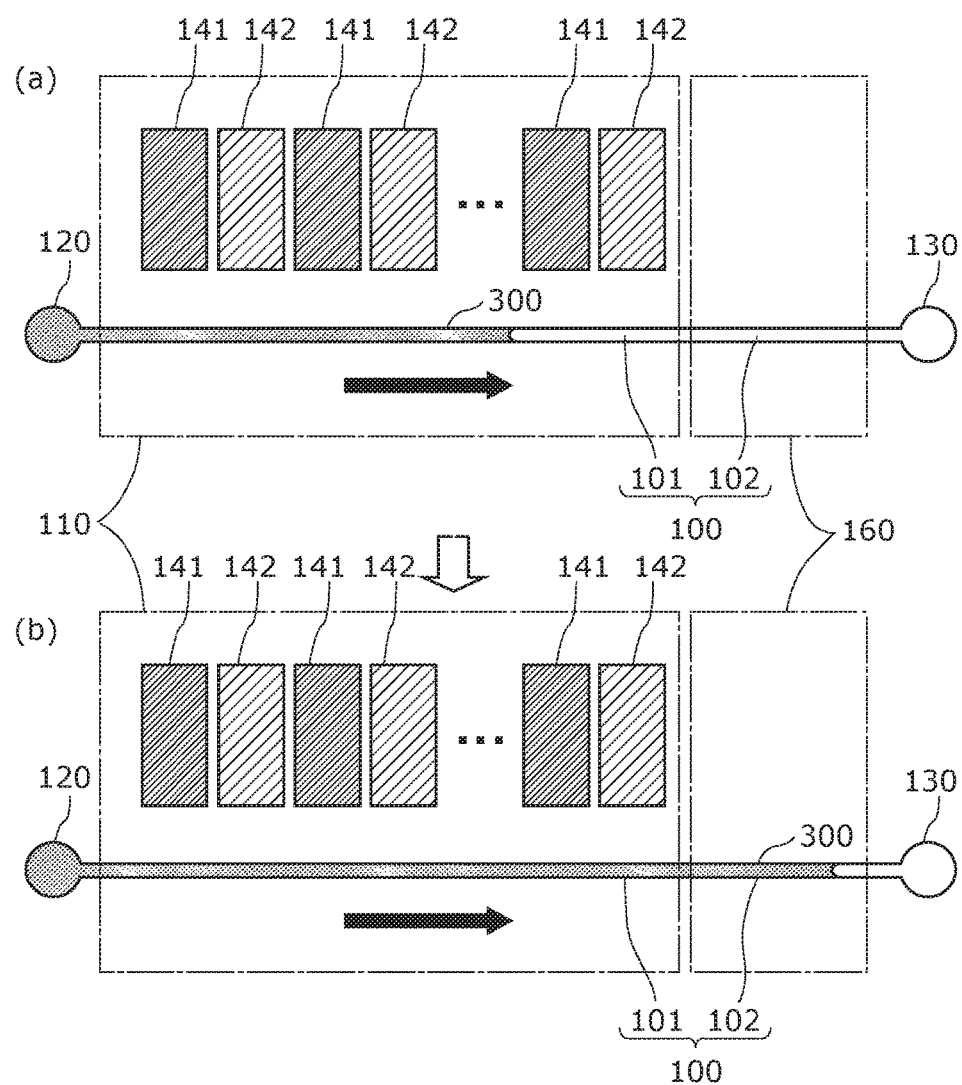
FIG. 26 illustrates in (a) and (b) the temperature cycle in a nucleic acid amplification device according to Embodiment 3 of the present invention.

Next, the nucleic acid amplification method using the nucleic acid amplification device 3 according to the present embodiment will be described using FIG. 26, with reference to FIG. 24A through FIG. 25. FIG. 26 illustrates the temperature cycle in the nucleic acid amplification device according to Embodiment 3 of the present invention, where (a) illustrates the fluid front of the reaction solution passing through the nucleic acid amplification reaction section and (b) illustrates the fluid front of the reaction solution passing through the fed solution retention section.

First, the target nucleic acid sample and the reagent for amplifying the target nucleic acid are introduced into the introduction unit 120 of the nucleic acid amplification device 3. More specifically, similar to Embodiment 1, a premixed solution including the reagent and the reaction solution, which includes the target nucleic acid, is introduced into the introduction unit 120 of the nucleic acid amplification device 3 as the reaction solution 300.

As illustrated in FIG. 24B and (a) in FIG. 26, the reaction solution 300 introduced into the introduction unit 120 is fed from the introduction unit 120 to the nucleic acid amplification reaction section 110 via the channel 100.

In the nucleic acid amplification reaction section 110, the target nucleic acid included in the reaction solution 300 is amplified by subjecting the reaction solution 300 to cyclic temperature changes.

More specifically, the reaction solution 300 reaching the nucleic acid amplification reaction section 110 repeatedly passes back and forth through the first heater block 141 and the second heater block 142 as it flows through the channel 100 (the first channel 101), as illustrated in (a) in FIG. 26. In other words, similar to Embodiment 1, the reaction solution 300 sequentially and alternately passes through two temperature zones—the high temperature zone (the first heater block 141) and the low temperature zone (the second heater block 142) in the nucleic acid amplification reaction section 110—repeatedly. With this, since the reaction solution 300 flowing through the channel 100 (the first channel 101) can be subjected to a heat cycle, substantially rapid PCR by flow can be achieved. Thus, the target nucleic acid included in the reaction solution 300 can be rapidly amplified.

Thereafter, as illustrated in FIG. 24B and (b) in FIG. 26, the reaction solution 300 is fed through the fed solution retention section 160 to the discharge unit 130. In other words, a fixed portion from the fluid front of the reaction solution 300 can be retained in the fed solution retention section 160. More specifically, a portion of the reaction solution 300 from a fixed length backward from the portion present in the discharge unit 130 (the front portion) is retained in the fed solution retention section 160.

In the present embodiment, when the fluid front of the reaction solution 300 introduced into the introduction unit 120 reaches the discharge unit 130, introduction of the solution including the target nucleic acid (referred to as the reaction solution in the present embodiment) into the introduction unit 120 is interrupted, which results in the channel 100 being completely filled with the reaction solution 300.

In the present embodiment as well, the reaction solution 300 is fed through the channel 100 by capillary force. For example, the reaction solution 300 can be fed by capillary force by giving the inner surfaces of the channel 100 (the first channel 101, the second channel 102) a hydrophilic surface with an acute contact angle.

[Advantageous Effects and Experimental Example]

Next, using FIG. 27A and FIG. 27B, advantageous effects of the nucleic acid amplification device 3 according to the present embodiment will be described along with the underlying knowledge that formed the basis of the present invention and an experimental example.

Figure 27A:
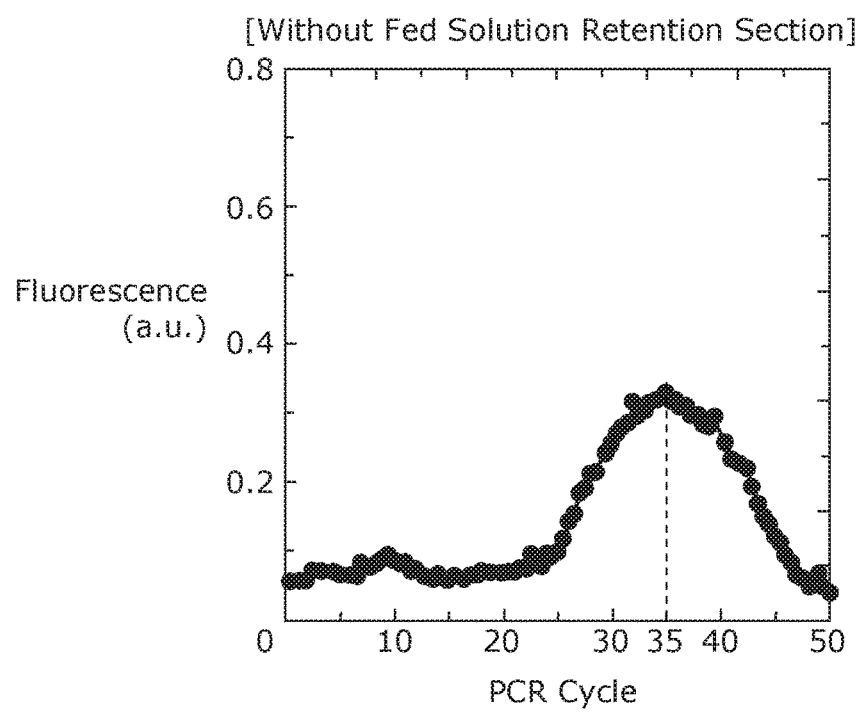
FIG. 27A illustrates the relationship between the PCR cycle of the reaction solution and fluorescence (amplification amount) when nucleic acid amplification is performed using a nucleic acid amplification device according to a comparative example.

FIG. 27A illustrates the relationship between the PCR cycle of the reaction solution and fluorescence (amplification amount) when nucleic acid amplification is performed using a nucleic acid amplification device according to a comparative example. FIG. 27B illustrates the relationship between the PCR cycle of the reaction solution and fluorescence (amplification amount) when nucleic acid amplification is performed using the nucleic acid amplification device according to Embodiment 3 and illustrated in FIG. 24A.

The nucleic acid amplification device according to the comparative example has a structure in which the fed solution retention section 160 (the second channel 102) in the nucleic acid amplification device 3 illustrated in FIG. 24A is omitted. Moreover, in both FIG. 27A and FIG. 27B, a reaction solution including human genome β-actin as the reaction sample (PCR reagent) was used, and the amplification amount of nucleic acid was calculated based on fluorescence using the nucleic acid amplification apparatus described above and illustrated in FIG. 15.

As illustrated in FIG. 27A, when the nucleic acid amplification device according to the comparative example is used, it can be seen that fluorescence increases in accordance with an increase in PCR cycles (in other words, the amount of nucleic acid increases), but when the PCR cycles exceed a given number of cycles, the fluorescence decreases (in other words, the amount of nucleic acid decreases). More specifically, the fluorescence was found to decrease after 35 PCR cycles out of a total of 50 PCR cycles.

This is believed to be because the front portion of the reaction solution fed through the channel reduces in reaction efficiency due to adsorption of the reagent to the channel wall surface or a change in concentration, for example, from evaporation of the reaction solution.

As illustrated by the nucleic acid amplification device according to the comparative example, conventional nucleic acid amplification devices have a problem that accurate amplification of the reaction solution is difficult.

In view of this, the Inventors of the present invention thought it possible to accurately amplify the target nucleic acid in the reaction solution by separating the front portion of the reaction solution, which has a low reaction efficiency, from the reaction solution capable of obtaining a desired efficiency.

More specifically, as illustrated in FIG. 24A and FIG. 24B, the Inventors of the present invention discovered providing the fed solution retention section 160 downstream the nucleic acid amplification reaction section 110 and retaining the front portion of the reaction solution, which has a low reaction efficiency, in the fed solution retention section 160. With this, the front portion of the reaction solution fed through the channel 100 can be advanced to the fed solution retention section 160 without stagnating in the nucleic acid amplification reaction section 110 and retained in the fed solution retention section 160.

As a result, the front portion of the reaction solution, which has a low reaction efficiency, can be separated from the reaction solution capable of obtaining a desired efficiency. In other words, by retaining the front portion of the reaction solution, which has a low reaction efficiency, in the fed solution retention section 160, the rear portion of the reaction solution, with which a desired efficiency is obtainable, can be retained in the nucleic acid amplification reaction section 110 without a decrease in reaction efficiency.

In this way, by providing the fed solution retention section 160, the front portion of the reaction solution, which has a low reaction efficiency, can be removed from the nucleic acid amplification reaction section 110, and a desired fluorescence (signal value) can be secured even when continuing to increase the PCR cycles.

Figure 27B:
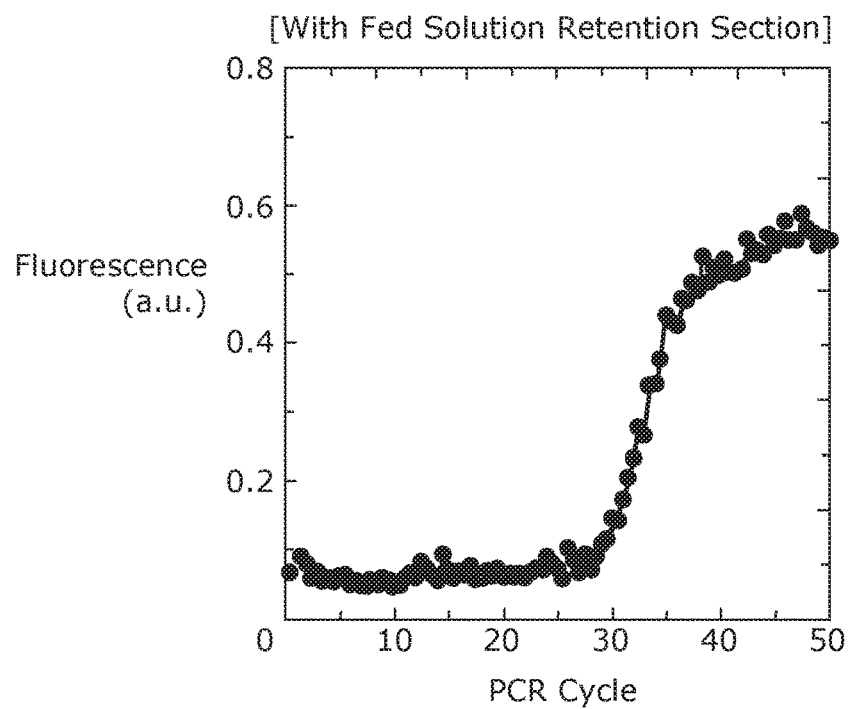
FIG. 27B illustrates the relationship between the PCR cycle of the reaction solution and fluorescence (amplification amount) when nucleic acid amplification is performed using a nucleic acid amplification device according to Embodiment 3 of the present invention.

When the nucleic acid amplification device 3 including the fed solution retention section 160 is used, the fluorescence actually increases rather than decreases in accordance with an increase in PCR cycles, as illustrated in FIG. 27B.

In other words, this shows that the amount of nucleic acid continues to increase in accordance with an increase in PCR cycles.

Moreover, as illustrated in FIG. 27A, when the fed solution retention section 160 is not provided, reaction efficiency decreases during the last 15 cycles of all the PCR cycles (50 cycles) (15/30=30%). Thus, when a histogram of the target nucleic acid in the reaction solution is used, the volumetric capacity of the second channel 102 may be 30% or more of the total volumetric capacity of the channel 100.

Note that in FIG. 27A, the maximum number of cycles is 50 cycles, but according to the results of the experimentation, even when the maximum number of cycles was 60 cycles or 70 cycles, the decrease in reaction efficiency was found to occur 15 cycles back from the fluid front. This trend is believed to hold true even when the maximum number of cycles is 150 cycles, at least.

Thus, in order to appropriately remove the front portion of the reaction solution, the volumetric capacity of the channel 100 in the fed solution retention section 160 (the second channel 102) may be at least 10% or more of the total volumetric capacity of the channel 100. In other words, the cubic volume of the reaction solution retained in the fed solution retention section 160 (retention cubic volume) may be 10% or more of the total cubic volume of the reaction solution filling the entire channel 100. With this, as illustrated in FIG. 27B, the target nucleic acid can be accurately amplified without observing a decrease in reaction efficiency.

Figure 28:
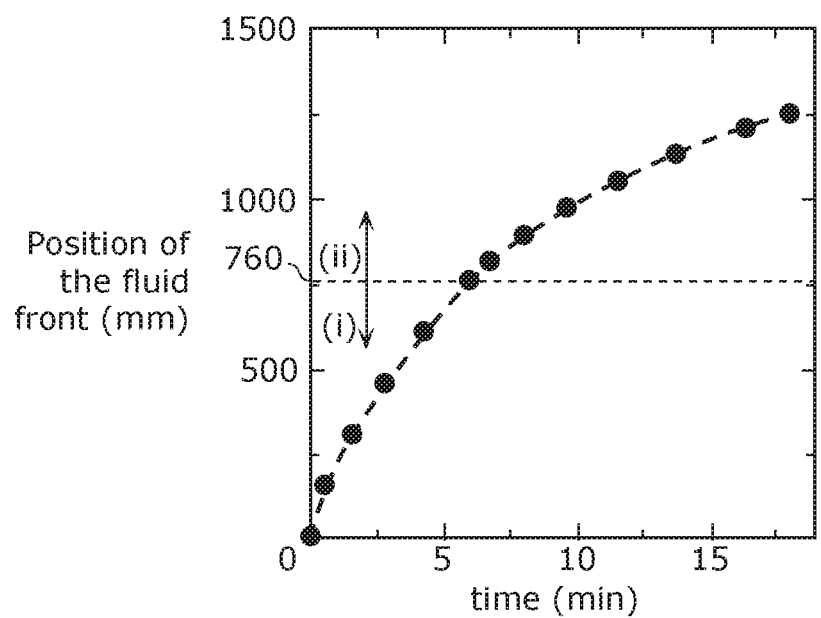
FIG. 28 illustrates the relationship between feed time and the position of the fluid front when the reaction solution is fed using a nucleic acid amplification device according to Embodiment 3 of the present invention.

Next, the feeding characteristics of the nucleic acid amplification device 3 according to the present embodiment will be described using FIG. 28. FIG. 28 illustrates the relationship between feed time and the position of the fluid front when the reaction solution is fed using the nucleic acid amplification device according to Embodiment 3 of the present invention. Note that the feed time is the time from the beginning of the feeding, and the position of the fluid front is the position of the front (fluid front) of the reaction solution in the channel. Moreover, a solution including β-actin detection reagents (Life Technologies Corporation) and human genome DNA was used as the reaction sample.

As illustrated in FIG. 28, in the region from 0 mm to 760 mm (region (i)), the fluid front of the reaction solution was positioned in the nucleic acid amplification reaction section 110, and in the region from 760 mm to 1260 mm (region (ii)), the fluid front of the reaction solution was positioned in the fed solution retention section 160.

Moreover, the reaction solution filled the nucleic acid amplification reaction section 110 in 6 minutes, and thereafter filled the fed solution retention section 160 in 12 minutes.

As a result, the average feeding velocity in the fed solution retention section 160 was approximately 0.68 mm/s. In the present embodiment, by controlling feeding of the subsequent reaction solution with the fed solution retention section 160, an efficient nucleic acid amplification reaction was achieved.

Next, results of an experimentation to evaluate the amplification characteristics of the nucleic acid amplification device 3 according to the present embodiment will be described using FIG. 29, FIG. 30, and FIG. 31.

Figure 29:
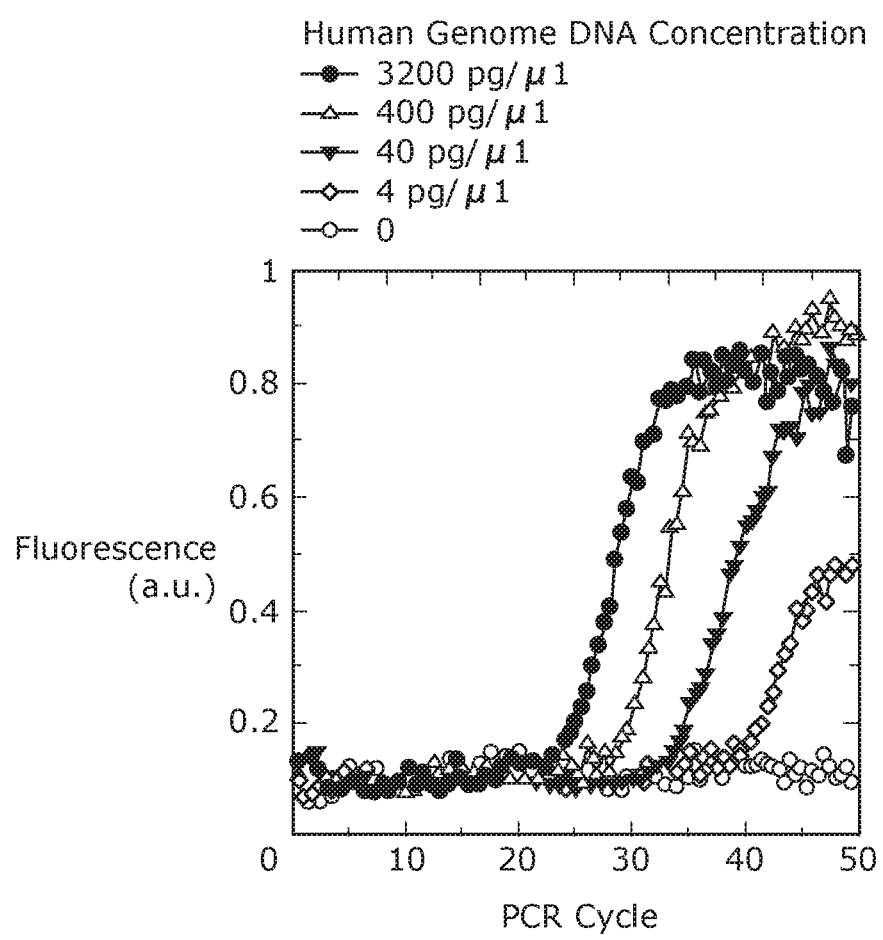
FIG. 29 illustrates the relationship between the PCR cycle of the reaction solution and fluorescence (amplification amount) when nucleic acid amplification is performed using a nucleic acid amplification device according to Embodiment 3 of the present invention.

FIG. 29 illustrates the relationship between the reaction solution PCR cycle and fluorescence (amplification amount) when nucleic acid amplification was performed using the nucleic acid amplification device according to Embodiment 3 of the present invention, and shows the optical detection results when measurement was performed by the nucleic acid amplification apparatus described above and illustrated in FIG. 15.

In this experimentation as well, a solution including β-actin detection reagents (Life Technologies Corporation) and human genome DNA was used as the reaction sample.

Also, as the DNA concentration, evaluation of amplification characteristics was performed for each of final concentrations of 3200 pg/ul, 400 pg/ul, 40 pg/ul, 4 pg/ul. Evaluation of amplification characteristics was also performed with a solution that did not include human genome DNA as a negative control (NC).

As illustrated in FIG. 29, in all of the human genome DNA concentrations, fluorescence increased with an increase in the PCR cycles—that is to say, the amount of nucleic acid increased.

Figure 30:
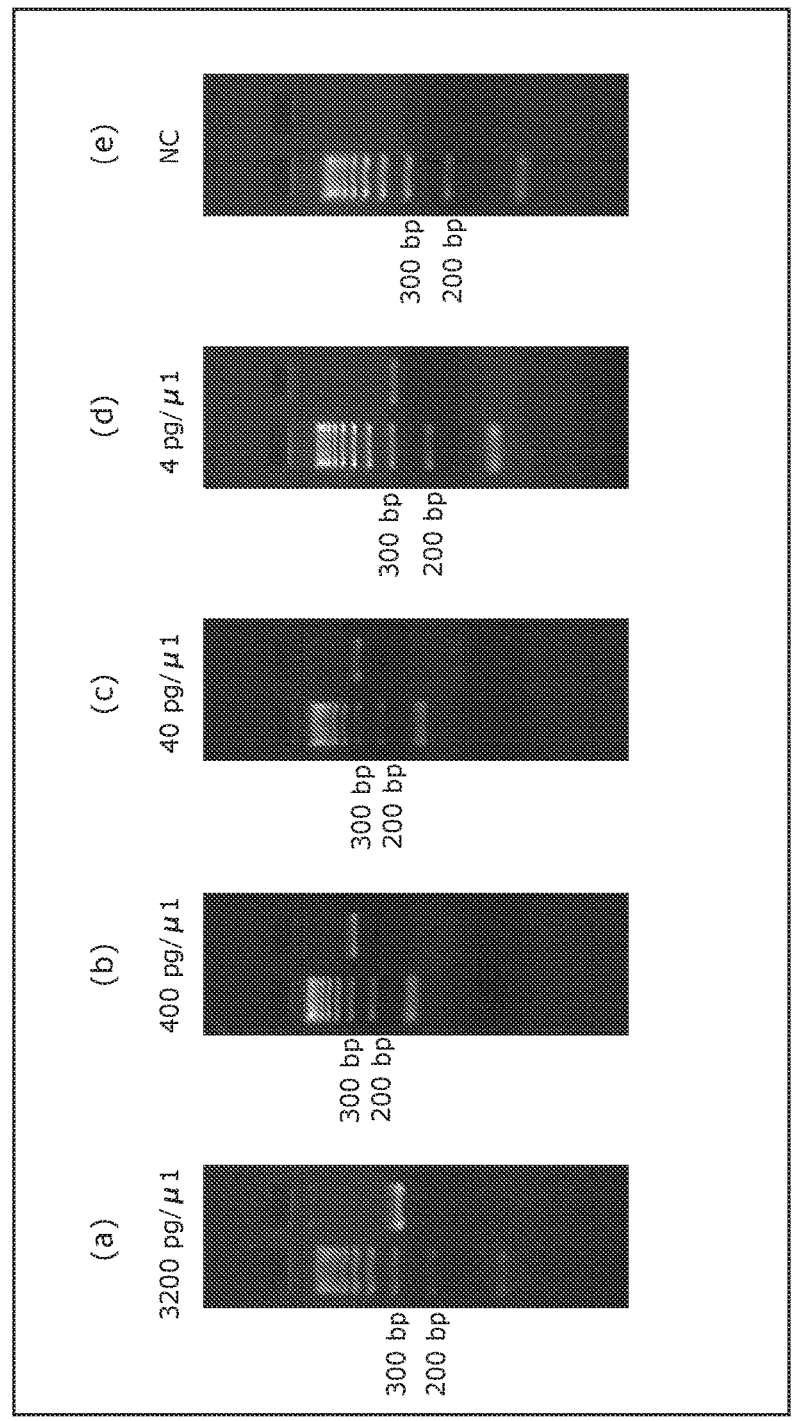
FIG. 30 illustrates in (a)-(e) gel electrophoresis images of standard DNA markers before and after amplification with respect to the initial concentration of the human genome DNA when nucleic acid amplification is performed using a nucleic acid amplification device according to Embodiment 3 of the present invention.

FIG. 30 illustrates gel electrophoresis images of standard DNA markers before and after amplification with respect to the initial concentration of the human genome DNA in FIG. 29. In FIG. 30, (a), (b), (C), (d), and (e) are images of human genome DNA final concentrations of 3200 pg/ul, 400 pg/ul, 40 pg/ul, 4 pg/ul, and 0 pg/ul (NC), respectively.

As illustrated in FIG. 30, for all initial concentrations, the DNA has been amplified a desired amount.

Figure 31:
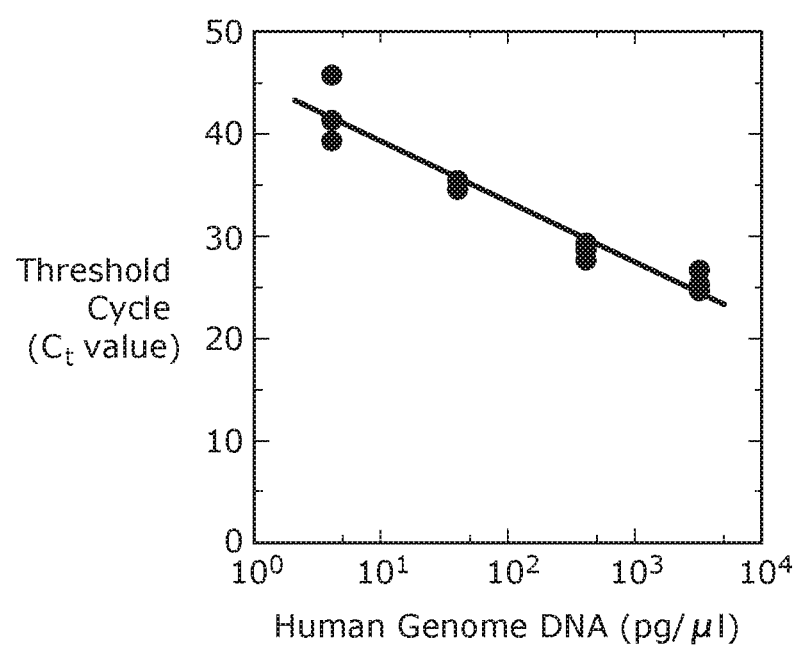
FIG. 31 illustrates the relationship between reaction sample (human genome DNA) concentration and the threshold cycle at start up when nucleic acid amplification is performed using a nucleic acid amplification device according to Embodiment 3.

FIG. 31 illustrates the relationship between reaction sample (human genome DNA) concentration in FIG. 29 and the threshold cycle at start up.

As illustrated in FIG. 31, the cycle at the PCR start up varies depending on the initial concentration of the human genome DNA. Thus, by defining the threshold cycle at start up as a cycle having a maximum value (saturation value) of approximately 10%, for example, a significantly linear calibration curve can be obtained, as illustrated in FIG. 31, and an initial concentration can be determined.

With the nucleic acid amplification device 3 according to the present embodiment, since the reaction solution can be fed by capillary force similar to Embodiments 1 and 2, the reaction solution can be advanced in the channel without the use of an external pump. Consequently, nucleic acid amplification of the target nucleic acid can be performed at low cost and easily.

Furthermore, the nucleic acid amplification device 3 according to the present embodiment includes, downstream the nucleic acid amplification reaction section 110, the fed solution retention section 160 for retaining the reaction solution. More specifically, the reaction solution fed from the first channel 101 disposed in the nucleic acid amplification reaction section 110 is retained in the second channel 102 disposed in the fed solution retention section 160.

With this, since the front portion of the reaction solution, which has a low reaction efficiency, can be removed from the nucleic acid amplification reaction section 110, the target nucleic acid included in the reaction solution can be accurately amplified.

Moreover, in the nucleic acid amplification device 3 according to the present embodiment, the reaction solution is fed through the channel 100 by capillary force.

With this, the reaction solution can be easily fed without the use of an external pump such as a syringe pump. Consequently, nucleic acid amplification of the target nucleic acid can be performed at low cost.

Moreover, in the nucleic acid amplification device 3 according to the present embodiment, the nucleic acid amplification reaction section 110 has at least two or more temperature zones of different temperature, and the channel 100 passes back and forth or in a cyclic fashion through these two or more temperature zones.

With this, since PCR by flow can be achieved, nucleic acid can be rapidly amplified.

Moreover, in the nucleic acid amplification device 3 according to the present embodiment, the channel 100 in the fed solution retention section 160 (the second channel 102) includes a meandering charnel.

With this, a relatively large volumetric capacity second channel 102 can be provided in a small space. Thus, the reaction solution can be retained in a compact space.
(Variations)

Hereinafter, variations of the nucleic acid amplification device according to Embodiment 3 of the present invention will be described. Note that the nucleic acid amplification device described below has the same structure as the nucleic acid amplification device according to the above-described Embodiment 3, and in each variation, only the characterizing configurations will be discussed.

Variation 1 of Embodiment 3

Figure 32:
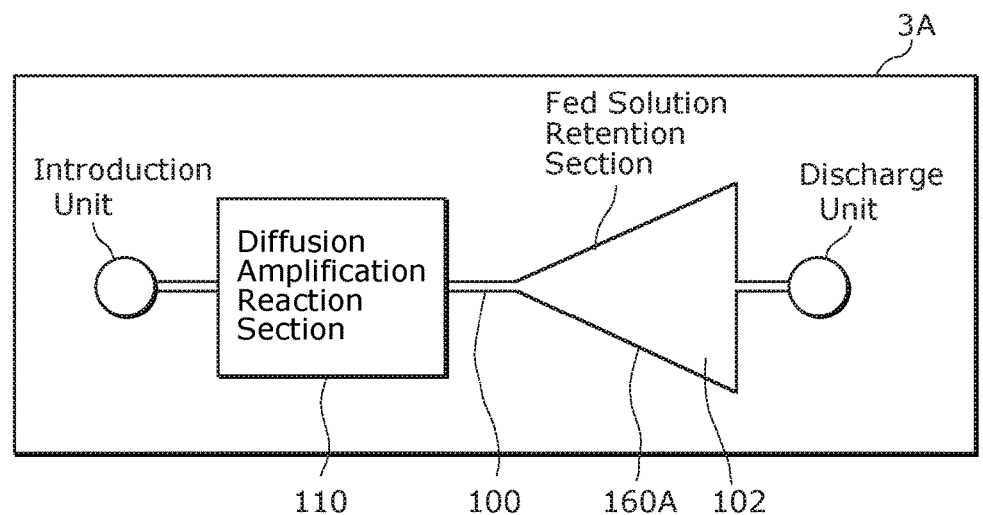
FIG. 32 is a schematic view of a nucleic acid amplification device according to Variation 1 of Embodiment 3 of the present invention.

FIG. 32 is a schematic view of the nucleic acid amplification device according to Variation 1 of Embodiment 3 of the present invention.

As illustrated in FIG. 32, with the nucleic acid amplification device 3A according to the present variation, the channel 100 (the second channel 102) in the fed solution retention section 160A includes an enlarged cross-sectional area section (enlarged cross-sectional area region) that gradually increases in cross-sectional area in the feeding direction of the reaction solution.

More specifically, the channel 100 (the second channel 102) in the enlarged cross-sectional area section of the fed solution retention section 160A has a tapered shape whose width gradually widens in a direction from upstream to downstream. Note that in the present variation, the channel 100 in the enlarged cross-sectional area section of the fed solution retention section 160A has a constant depth.

In this way, with the nucleic acid amplification device 3A according to the present variation, the cross-sectional area of the channel 100 (the second channel 102) in the fed solution retention section 160A gradually increases. With this, a large volume of reaction solution can be smoothly fed. Thus, the reaction solution can be retained in the fed solution retention section 160A for a small amount of time.

Variation 2 of Embodiment 3

Figure 33:
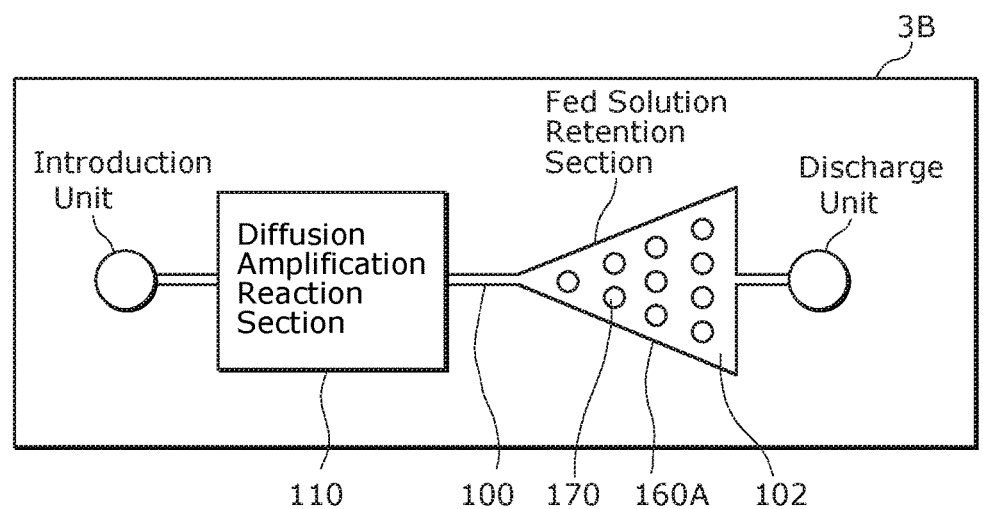
FIG. 33 is a schematic view of a nucleic acid amplification device according to Variation 2 of Embodiment 3 of the present invention.

FIG. 33 is a schematic view of the nucleic acid amplification device according to Variation 2 of Embodiment 3 of the present invention.

As illustrated in FIG. 33, the fed solution retention section 160B in the nucleic acid amplification device 3B according to the present variation has an enlarged cross-sectional area section, similar to the fed solution retention section 160A according to Variation 1.

In the present variation, the enlarged cross-sectional area section of the fed solution retention section 160B (the second channel 102) further includes a plurality of pillars 170. Each pillar 170 has, for example, a cylindrical shape in a plan view, and is disposed upright in the second channel 102.

In this way, in the nucleic acid amplification device 3B according to the present variation, the enlarged cross-sectional area section of the fed solution retention section 160B (the second channel 102) includes a plurality of pillars 170. With this, the feeding surface of the fluid front of the reaction solution can be made to be uniform in a plane. Thus, since the generation of air bubbles in the second channel 102 can be inhibited, the feeding of the reaction solution can be stabilized.

In other words, when pillars are not provided such as in FIG. 32, since the closer the reaction solution is to the hydrophilic wall surface of the second channel 102, the further forward the reaction solution advances forward along the wall surface, pockets (air bubbles) easily generate in the central portion of the second channel 102, but when the plurality of pillars 170 are provided, the reaction solution close to the wall surface of the second channel 102 can be inhibited from being fed ahead, so the feeding surface of the fluid front of the reaction solution can be made to be uniform.

Variation 3 of Embodiment 3

Figure 34:
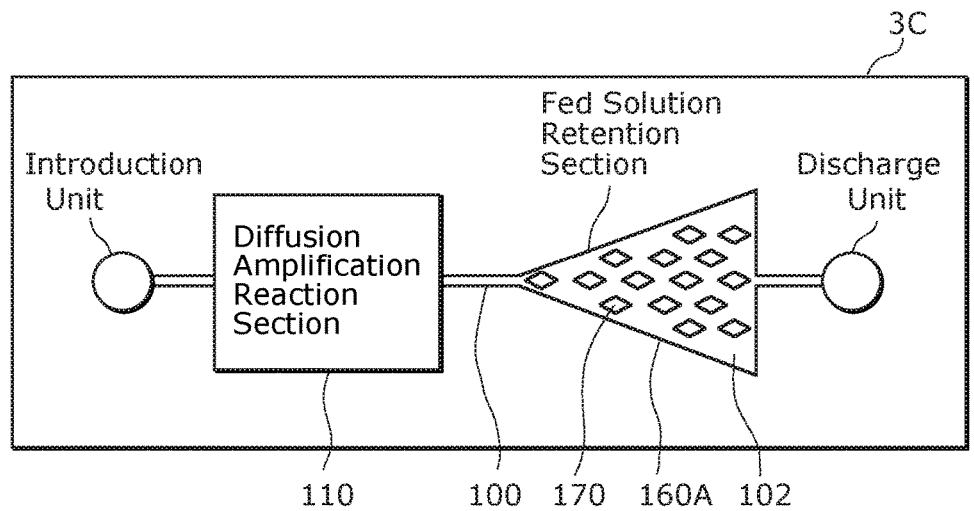
FIG. 34 is a schematic view of a nucleic acid amplification device according to Variation 3 of Embodiment 3 of the present invention.

FIG. 34 is a schematic view of the nucleic acid amplification device according to Variation 3 of Embodiment 3 of the present invention.

As illustrated in FIG. 34, similar to the fed solution retention section 160B according to Variation 2, the fed solution retention section 160C in the nucleic acid amplification device 3C according to the present variation has an enlarged cross-sectional area section and includes a plurality of pillars 170.

Furthermore, in the present variation, the plurality of pillars 170 are aligned with regularity, and each of the plurality of pillars 170 has an approximate diamond shape in a plan view. With this, the feeding surface of the fluid front of the reaction solution can be made to be uniform.

Note the plan view approximate diamond shape is not limited to a diamond shape, and includes diamond shapes with rounded corners.

Variation 4 of Embodiment 3

Figure 35:
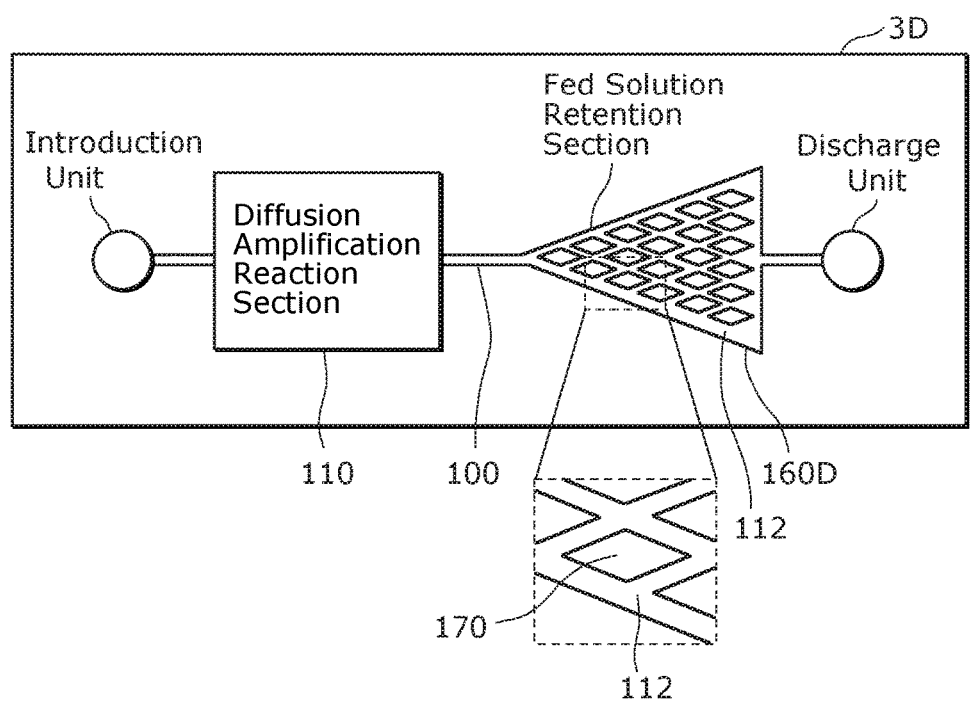
FIG. 35 is a schematic view of a nucleic acid amplification device according to Variation 4 of Embodiment 3 of the present invention.

FIG. 35 is a schematic view of the nucleic acid amplification device according to Variation 4 of Embodiment 3 of the present invention.

As illustrated in FIG. 35, similar to the fed solution retention section 160C according to Variation 3, the fed solution retention section 160D in the nucleic acid amplification device 3D according to the present variation has an enlarged cross-sectional area section and includes a plurality of pillars 170 having an approximate diamond shape in a plan view.

Furthermore, in the present variation, one side of each of the plurality of pillars 170 is substantially parallel to a side wall of the second channel 102 in the enlarged cross-sectional area section of the fed solution retention section 160D. With this, the feeding surface of the fluid front of the reaction solution can be further made to be uniform.

Moreover, in the present variation, the plurality of pillars 170 are evenly spaced from one another. With this, the feeding surface of the fluid front of the reaction solution can be made to be more uniform.

Variation 5 of Embodiment 3

Figure 36:
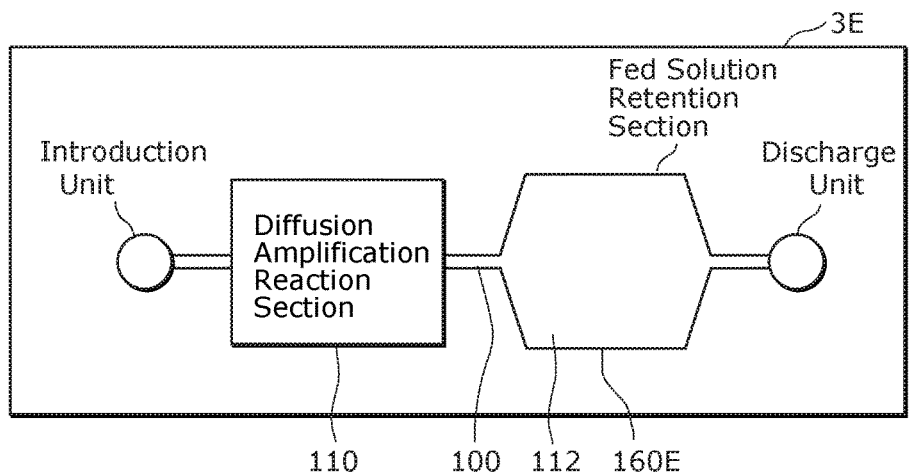
FIG. 36 is a schematic view of a nucleic acid amplification device according to Variation 5 of Embodiment 3 of the present invention.

FIG. 36 is a schematic view of the nucleic acid amplification device according to Variation 5 of Embodiment 3 of the present invention.

As illustrated in FIG. 36, in the fed solution retention section 160E in the nucleic acid amplification device 3E according to the present variation, the second channel 102 has a cross-sectional area greater than the cross-sectional area of the channel 100 (the first channel) in the nucleic acid amplification reaction section 110. With this, a large volume of reaction solution can be retained in a compact space in the fed solution retention section 160 (the second channel).

Variation 6 of Embodiment 3

Figure 37:
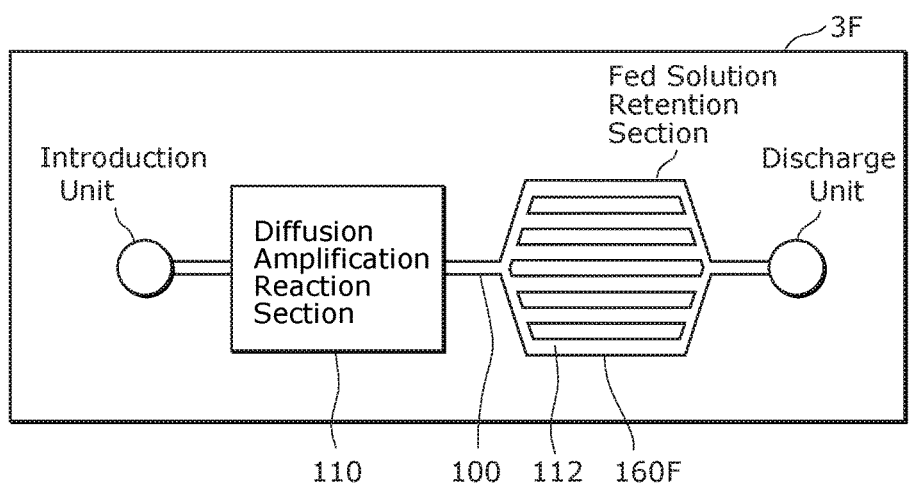
FIG. 37 is a schematic view of a nucleic acid amplification device according to Variation 6 of Embodiment 3 of the present invention.

FIG. 37 is a schematic view of the nucleic acid amplification device according to Variation 6 of Embodiment 3 of the present invention.

As illustrated in FIG. 37, in the fed solution retention section 160F in the nucleic acid amplification device 3F according to the present variation, a portion of the second channel 102 is divided into branches. Note that in the present variation, the second channel 102 is divided into six branches, but this example is not limiting. For example, the second channel 102 may be divided into two branches and have a Y shape, or may be divided into a different number of branches.

In this way, by dividing a portion of the second channel 102 into a plurality of branches to produce a plurality of second channels 102, smooth connection with the channel 100 is possible and a large volume of reaction solution can be retained in a compact space in the fed solution retention section 160.

(Other Variations)

Hereinafter, other variations of the nucleic acid amplification device according to the above embodiments will be described.

(Variation 1)

Figure 38:
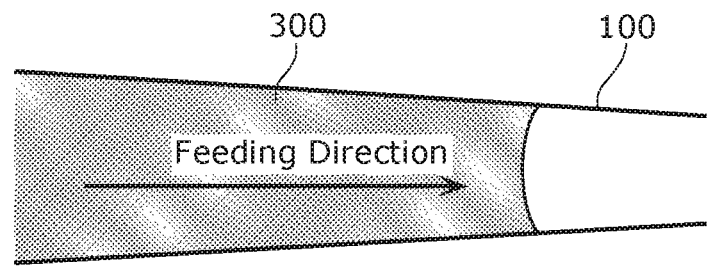
FIG. 38 is an enlarged plan view of a channel in a nucleic acid amplification device according to Variation 1 of the present invention.

FIG. 38 is an enlarged plan view of a channel in the nucleic acid amplification device according to Variation 1 of the present invention.

In the nucleic acid amplification device according to the present variation, the portion of the channel 100 in at least the nucleic acid amplification reaction section 110 includes a region having a cross-sectional area that decreases in the feeding direction. With this configuration, the feeding velocity of the reaction solution 300 can be made to be constant.

More specifically, as illustrated in FIG. 38, the channel 100 has a tapered structure whose depth is constant and width gradually decreases such that the cross-sectional area of the channel 100 monotonically decreases. Note that the channel 100 may have a tapered structure whose width is constant and depth gradually decreases.

With this configuration, since pressure loss and capillary pressure can be continually varied, feeding velocity of the reaction solution can be made to be even more constant.

Moreover, with the present variation, since the channel 100 has a constant depth, the channel 100 can be easily formed in one process by, for example, etching. Furthermore, since the channel 100 has a constant depth, when taking optical measurements by scanning laser light across the above-described channel 100, the length of the measurement light path can be kept constant. This makes it possible to increase measurement accuracy. This makes it possible to, for example, accurately calculate the amplification amount of nucleic acid.

(Variation 2)

Figure 39:
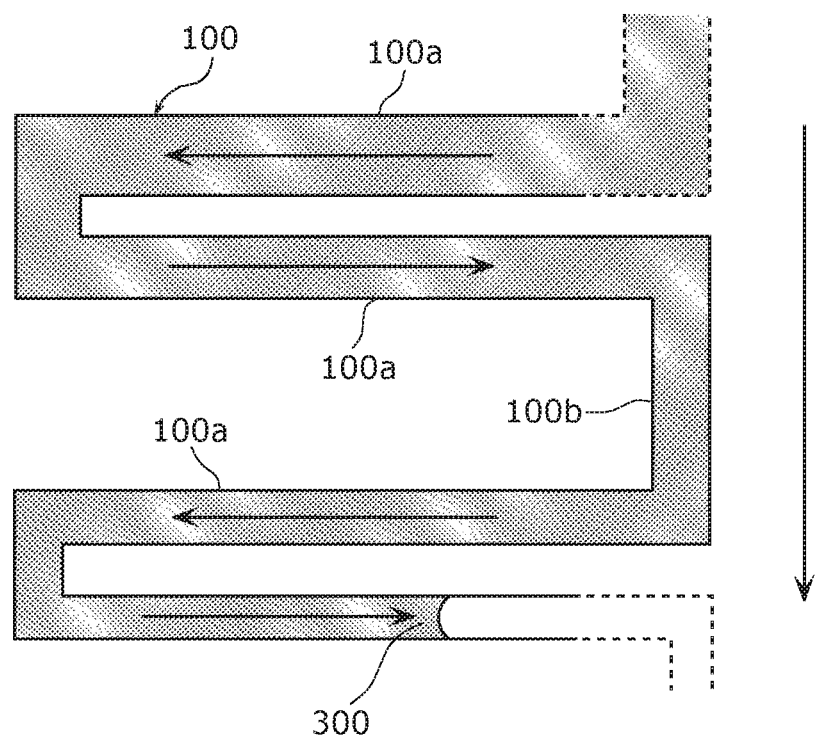
FIG. 39 is an enlarged plan view of a channel in a nucleic acid amplification device according to Variation 2 of the present invention.

FIG. 39 is an enlarged plan view of a channel in the nucleic acid amplification device according to Variation 2 of the present invention.

Similar to Variation 1, in the nucleic acid amplification device according to the present variation, the portion of the channel 100 in at least the nucleic acid amplification reaction section 110 includes a region having a cross-sectional area that decreases in the feeding direction. With this, the feeding velocity of the reaction solution can be made to be constant.

The point of difference with Variation 1 is that according to the present variation, the channel 100 in the region having a decreasing cross-sectional area is configured of a plurality of line-shaped meandering main channels 100a, and the cross-sectional area of these main channels 100a decreases with each line in the feeding direction. In the present variation, the cross-sectional area of the channel 100 is decreased by forming the main channels 100a to be narrower (in width) with each line in the feeding direction. Note that the width and depth of each individual line of the main channel 100a is constant.

With this configuration, since the channel 100 can be formed in straight lines, the design and formation of the channel 100 is simpler than Variation 1. Furthermore, since the channel 100 has a constant depth, the channel 100 can be easily formed in one process by, for example, etching, and when taking optical measurements by scanning laser light across the above-described channel 100, the length of the measurement light path can be kept constant, and therefore measurement accuracy can be increased.

(Variation 3)

Figure 40:
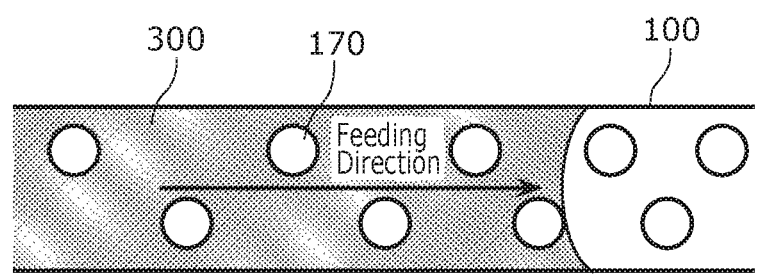
FIG. 40 is an enlarged plan view of a channel in a nucleic acid amplification device according to Variation 3 of the present invention.

FIG. 40 is an enlarged plan view of a channel in the nucleic acid amplification device according to Variation 3 of the present invention.

Similar to Variation 1, in the nucleic acid amplification device according to the present variation, the portion of the channel 100 in at least the nucleic acid amplification reaction section 110 includes a region having a cross-sectional area that decreases in the feeding direction. With this, the feeding velocity of the reaction solution can be made to be constant.

The point of difference with Variation 1 is that according to the present variation, the cross-sectional area of the channel 100 in the region having a decreasing cross-sectional area is adjusted by disposing pillars 170, as illustrated in FIG. 40.

More specifically, by disposing cylindrical pillars 170 upright in the channel 100 at predetermined distances from one another, the cross-sectional area of the channel 100 in the feeding direction can be made to sectionally decrease.

With this configuration, the feeding velocity of the reaction solution can be adjusted. Moreover, providing the pillars 170 makes it possible to increase the diffusion of the sample and the reagent in the reaction solution.

(Variation 4)

Figure 41:
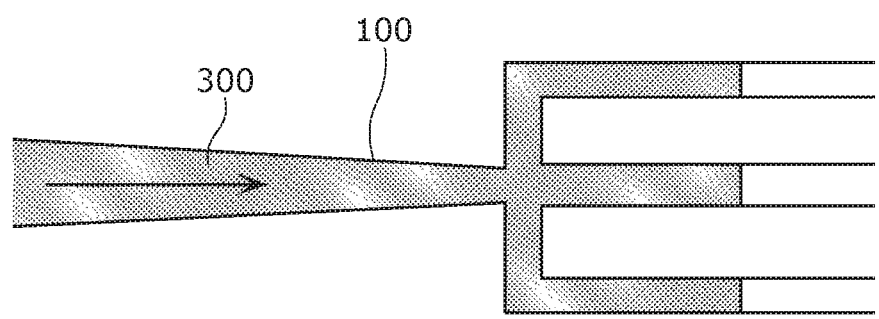
FIG. 41 is an enlarged plan view of a channel in a nucleic acid amplification device according to Variation 4 of the present invention.

FIG. 41 is an enlarged plan view of a channel in the nucleic acid amplification device according to Variation 4 of the present invention.

In the nucleic acid amplification device according to the present variation, a portion of the channel 100 is divided into branches. More specifically, as illustrated in FIG. 41, the tip of the channel 100 having a tapered structure is divided into three branches.

By dividing a portion of the channel 100 into branches in this manner, the feeding velocity of the fluid front (front portion) of the reaction solution 300 can be controlled and additionally the feeding velocity of the internal portion of the reaction solution 300 can be controlled.

(Other Points)

Although the nucleic acid amplification device, nucleic acid amplification method, etc., according to the present invention have been described based on the above embodiments and variations, the present invention is not limited to the above embodiments and variations.

For example, in the above embodiments and variations, a PCR by flow technique in which the channel 100 in the nucleic acid amplification reaction section 110 is a meandering channel and the reaction solution including the target nucleic acid is repeatedly subjected to temperature change is used, but a PCR technique in which the reaction solution including the target nucleic acid is repeatedly subjected to temperature change may be used instead of a PCR by flow technique. However, in the above embodiments, employing a flow technique yields a more efficient PCR.

Moreover in the above embodiments and variations, the channel 100 is a meandering channel, but the channel 100 is not limited to this example. For example, a configuration is acceptable in which a plurality of high temperature zones (95° C.) and a plurality of low temperature zones (60° C.) may be alternately arranged in a linear shape, and a substrate having a line-shaped channel may be disposed thereon to make the channel alternately pass through the high temperature zone and the low temperature zone.

Moreover, in the above embodiments and variations; the heater unit 140 includes two temperature zones, but the heater unit 140 may include three or more temperature zones of mutually different temperatures. In this case, the channel may be configured such that the reaction solution passes through the plurality of different temperature zones in a cyclic fashion.

Moreover in the above embodiments and variations, the setting of the temperature for each of the plurality of temperature zones was achieved with heat blocks, but a different temperature control component such as a Peltier device may be used to set the temperature.

Various modifications of the exemplary embodiments as well as embodiments resulting from arbitrary combinations of elements of different embodiments conceivable by those skilled in the art are intended to be included within the scope of the present invention as long as they do not depart from the essence of the present invention.

REFERENCE SIGNS LIST 1, 2, 2A, 2B, 2C, 2D, 3, 3A, 3B, 3C, 3D, 3E, 3F nucleic acid amplification device
10 first substrate
11 first recessed portion
12 second recessed portion
13 groove
14, 24 hydrophilic film
15 silicon oxide film
20 second substrate
21 first through-hole
22 second through-hole
100 channel
100a main channel
100b sub channel
100c introduction channel
100d discharge channel
101 first channel
102 second channel
110 nucleic acid amplification reaction section
120 introduction unit
120a first introduction unit
120b second introduction unit
130 discharge unit
140 heater unit
141 first heater block
142 second heater block
150 mixing unit
160, 160A, 160B, 160C, 160D, 160E, 160F fed solution retention section
170 pillar
200 nucleic acid amplification apparatus
210 temperature control unit
220 detection unit
221 light output unit
222 light receptor unit
223 optical scanning unit
224 excitation cut filter
225 dichroic mirror
300 reaction solution

The invention claimed is:

1. A nucleic acid amplification device comprising:
an introduction unit into which a reaction solution including a target nucleic acid is introduced;
a nucleic acid amplification reaction section including at least two temperature zones of different temperature, for amplifying the target nucleic acid included in the reaction solution introduced into the introduction unit;
a channel arranged to pass back and forth or in cyclic fashion through the at least two temperature zones, and having a capillary force transport mechanism for feeding the reaction solution by capillary force;
a fed solution retention section for retaining the reaction solution; and
a discharge unit configured to discharge the reaction solution including the target nucleic acid after amplification,
wherein the channel includes a first channel disposed in the nucleic acid amplification reaction section and a second channel disposed in the fed solution retention section,
a first end of the second channel is connected to the first channel,
a second end of the second channel is connected to the discharge unit,
a volumetric capacity of the second channel is 10% or more of a total volumetric capacity of the channel, and
the second channel retains the reaction solution fed from the first channel.

2. The nucleic acid amplification device according to claim 1, wherein
the channel is connected to an external space only in the introduction unit and the discharge unit.

3. The nucleic acid amplification device according to claim 1, wherein
the channel has, as the capillary force transport mechanism, a wall surface that is a hydrophilic surface and has an acute contact angle.

4. The nucleic acid amplification device according to claim 3, wherein
wall surfaces around an entire perimeter of the channel in a cross section perpendicular to a feeding direction of the reaction solution are hydrophilic surfaces.

5. The nucleic acid amplification device according to claim 3, wherein
the hydrophilic surface of the channel is a surface of a hydrophilic film provided in the channel.

6. The nucleic acid amplification device according to claim 5, wherein
the hydrophilic film comprises a material including a hydrophilic group and a hydrophobic group.

7. The nucleic acid amplification device according to claim 6, wherein
the hydrophilic film comprises a surfactant.

8. The nucleic acid amplification device according to claim 7, wherein
the surfactant is a non-ionic surfactant.

9. The nucleic acid amplification device according to claim 1, wherein
the introduction unit comprises a plurality of introduction units,
the nucleic acid amplification device further comprises a mixer disposed between the nucleic acid amplification reaction section and the plurality of introduction units,
the plurality of introduction units are connected as one in the mixer via introduction channels corresponding to the plurality of introduction units, and
a plurality of solutions introduced via the plurality of introduction units mix together in the mixer to produce the reaction solution.

10. The nucleic acid amplification device according to claim 1, wherein
the channel includes, at least in the nucleic acid amplification reaction section, a region having a cross-sectional area that decreases in the feeding direction.

11. A nucleic acid amplification apparatus comprising:
the nucleic acid amplification device according to claim 1; and
a temperature controller configured to control a temperature of the nucleic acid amplification reaction section.

12. The nucleic acid amplification apparatus according to claim 11, further comprising
a detector configured to detect nucleic acid amplification of the target nucleic acid.

13. The nucleic acid amplification apparatus according to claim 12, wherein
the detector includes:
a light output configured to output light for irradiating the nucleic acid amplification device; and
a light receptor configured to receive reflected light of the light irradiating the nucleic acid amplification device.

14. The nucleic acid amplification apparatus according to claim 13, wherein
the detector further includes an optical scanner configured to scan the light over the channel of the nucleic acid amplification device.

15. A nucleic acid amplification method for amplifying a target nucleic acid using a nucleic acid amplification device, the nucleic acid amplification method comprising:

introducing the target nucleic acid and a reagent for amplifying the target nucleic acid into an introduction unit of the nucleic acid amplification device; and
as a reaction solution including the target nucleic acid and the reagent is fed by capillary force, amplifying the target nucleic acid included in the reaction solution,
wherein the nucleic acid amplification device includes a fed solution retention section for retaining the reaction solution, the fed solution retention section including a channel including a channel portion having a volumetric capacity that is 10% or more of a total volumetric capacity of the channel; and a discharge unit that discharges the reaction solution including the target nucleic acid after amplification, and
when a fluid front of the reaction solution fed by capillary force reaches the discharge unit, introduction of a solution including the target nucleic acid into the introduction unit is interrupted.

16. The nucleic acid amplification method according to claim 15, wherein
in the introducing, a premixed solution of (i) a solution including the target nucleic acid and (ii) the reagent is introduced into the nucleic acid amplification device as the reaction solution.

17. The nucleic acid amplification method according to claim 15, wherein
in the introducing, a first solution including the target nucleic acid and a second solution including the reagent are separately introduced into the nucleic acid amplification device, and
in the amplifying, as a solution of the first solution and the second solution mixed together in the nucleic acid amplification device is fed by capillary force as the reaction solution, the target nucleic acid included in the reaction solution is amplified.

18. The nucleic acid amplification method according to claim 15, wherein
in the amplifying, the target nucleic acid included in the reaction solution is amplified by subjecting the reaction solution to cyclic temperature changes.

19. The nucleic acid amplification apparatus according to claim 1, wherein the second channel includes a meandering path.

20. The nucleic acid amplification method according to claim 15, the channel portion including a meandering path.

* * * * *